(12) United States Patent
Alanine et al.

(10) Patent No.: US 6,451,819 B2
(45) Date of Patent: Sep. 17, 2002

(54) HETEROCYCLIC COMPOUNDS USEFUL AS NMDA RECEPTOR SELECTIVE SUBTYPE BLOCKERS

(75) Inventors: Alexander Alanine, Schlierbach (FR); Bernd Buettelmann, Schopfheim (DE); Marie-Paule Heitz Neidhart, Hagenthal le Bas (FR); Georg Jaeschke, Basel (CH); Emmanuel Pinard, Linsdorf (FR); Rene Wyler, Zuerich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/833,450

(22) Filed: Apr. 12, 2001

(30) Foreign Application Priority Data

Apr. 20, 2000 (EP) .............................. 00108610

(51) Int. Cl.[7] ................... A61K 31/435; A61K 31/445; C07D 207/12; C07D 401/04
(52) U.S. Cl. ...................... 514/326; 546/208; 548/556; 514/424
(58) Field of Search ................................ 514/326, 424; 546/208; 548/556

(56) References Cited

FOREIGN PATENT DOCUMENTS

| EP | 160 436 | 11/1985 |
|----|---------|---------|
| EP | 0 937 458 A2 | 8/1999 |
| WO | WO 97/23215 | 7/1997 |
| WO | WO 00/75109 A1 | 12/2000 |

OTHER PUBLICATIONS

Padwa et al., *J. Org. Chem*, vol. 52, pp. 235–244 (1987).

Primary Examiner—Ceila Chang
Assistant Examiner—Sonya Wright

(74) *Attorney, Agent, or Firm*—George W. Johnston; Patricia S. Rocha-Tramaloni; Arthur D. Dawson

(57) ABSTRACT

The invention relates to treating neurodegeneration by selective blocking of NMDA receptor with compounds of formula

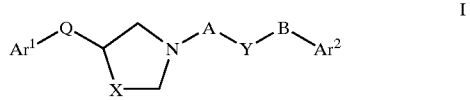

I wherein
Ar[1] is pyridyl or phenyl, substituted by hydroxy, lower alkyl, halogen, amino, nitro, benzyloxy or lower alkoxy-lower alkoxy, or is the group

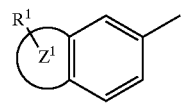

wherein
$Z^1$ is a five membered heterocyclic ring, which contains one or two heteroatoms, selected from N or O;
$R^1$ is hydrogen, hydroxy or an oxo group;
Ar[2] is pyridyl or phenyl, optionally substituted by hydroxy, lower alkyl, halogen, amino, nitro, benzyloxy or lower alkoxy-lower alkoxy, or is the group

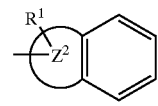

wherein
$Z^2$ is a five or six membered ring, which optionally contains one or two heteroatoms, selected from N or O; and
Q, X, A, Y B are as defined in the specification.

18 Claims, No Drawings

HETEROCYCLIC COMPOUNDS USEFUL AS NMDA RECEPTOR SELECTIVE SUBTYPE BLOCKERS

FIELD OF INVENTION

The present invention is generally related to heterocyclic compounds and more particularly to substituted heterocyclics useful as NDMA receptor selective subtype blockers for modulation neuronal activity and plasticity.

BACKGROUND

The present invention relates to compounds of the general formula

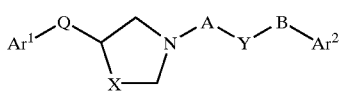

I wherein
$Ar^1$ is pyridyl or phenyl, substituted by hydroxy, lower alkyl, halogen, amino, nitro. benzyloxy or lower alkoxy-lower alkoxy, or is the group

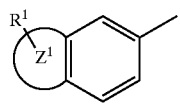

wherein
$Z^1$ is a five membered heterocyclic ring, which contains one or two heteroatoms, selected from N or O;
$R^1$ is hydrogen, hydroxy or an oxo group;
$Ar^2$ is pyridyl or phenyl, optionally substituted by hydroxy, lower alkyl, halogen, amino, nitro, benzyloxy or lower alkoxy-lower alkoxy, or is the group

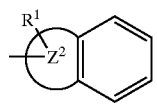

wherein
$Z^2$ is a five or six membered ring, which optionally contains one or two heteroatoms, selected from N or O; and
Q is —S—, —S(O)— or —S(O)$_2$—;
X is a bond, —CH(OH)— or —(CH$_2$)$_n$—;
A is a bond or —(CHR)$_m$—;
R is hydrogen, halogen or hydroxy, independently from each other if m is 2 or 3;
Y is —(CR$_2$)$_m$—, —O—, —C=C—, —C≡C—, piperidin-1-yl, pyrrolidin-1-yl or C$_4$–C$_6$-cycloalkyl, which rings are optionally substituted by hydroxy;
B is a bond, —O— or —(CHR)$_m$;
n is 1 or 2; and
m is 1, 2 or 3;
and to pharmaceutically acceptable acid addition salts thereof.

Excluded from the scope of formula I are those compounds, wherein A and B are simultaneously a bond and Y is —CHR—. These compounds have been described in EP 160 436, useful as antiarrythmic agents.

The present invention embraces racemic mixtures and all their corresponding enantiomers.

The compounds of formula I and their salts are distinguished by valuable therapeutic properties. Compounds of the present invention are NMDA (N-methyl-D-aspartate)-receptor subtype selective blockers, which have a key function in modulating neuronal activity and plasticity which makes them key players in mediating processes underlying development of CNS as well as learning and memory formation.

Under pathological conditions of acute and chronic forms of neurodegeneration over-activation of NMDA receptors is a key event for triggering neuronal cell death. NMDA receptors are composed of members from two sub-unit families, namely NR-1 (8 different splice variants) and NR-2 (A to D) originating from different genes. Members from the two sub-unit families show a distinct distribution in different brain areas. Heteromeric combinations of NR-1 members with different NR-2 sub-units result in NMDA receptors displaying different pharmaceutical properties. Possible therapeutic indications for NMDA receptor subtype specific blockers include acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis) and neurodegeneration associated with bacterial or viral infections, and, in addition, chronic and acute pain.

Objects of the invention are the compounds of formula I and pharmaceutically acceptable acid addition salts thereof, the preparation of the compounds of formula I and salts thereof, medicaments containing a compound of formula I or a pharmaceutically acceptable acid addition salt thereof, the manufacture of such medicaments and the use of the compounds of formula I and their pharmaceutically acceptable salts in the control or prevention of illnesses, especially of illnesses and disorders of the kind referred to earlier, and, respectively, for the manufacture of corresponding medicaments.

The following definitions of the general terms used in the present description apply irrespective of whether the terms in question appear alone or in combination.

As used herein, the term "lower alkyl" denotes a straight- or branched-chain alkyl group containing from 1 to 7 carbon atoms, for example, methyl, ethyl, propyl, isopropyl, butyl and the like. Preferred are groups from 1 to 4 carbon atoms.

The term "halogen" denotes chlorine, iodine, fluorine and bromine.

The term "lower alkoxy" denotes a group wherein the alkyl residue is as defined above.

A "five membered heterocyclic ring, which contains one or two heteroatoms, selected from N or O" denotes, for example, oxazolyl, isoxazolyl, furyl, pyrrolyl, pyrrolidinyl, pyrrolinyl, imidazolyl, imidazolidinyl, imidazolinyl, pyrazolyl, pyrazolidinyl or pyrazolinyl.

A "five or six membered ring, which optionally contains one or two heteroatoms, selected from N or O" are, for example; cyclopentyl, cyclohexyl, oxazolyl, isoxazolyl, furyl, pyrrolyl, pyrrolidinyl, pyrrolinyl, imidazolyl, imidazolidinyl, imidazolinyl, pyrazolyl, pyrazolidinyl, pyrazolinyl, pyridyl, pyrazinyl, pyrimidinyl, pyridazinyl, piperidyl, piperazinyl or morpholinyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of formula I in the scope of the present invention are those, wherein Ar¹ is phenyl, substituted by hydroxy, Q is —S—, Ar² is phenyl and X is —CH₂. These are the following compounds:

(S)-4-[1-(4-phenyl-butyl)-pyrrolidin-3-yl-sulfanyl]-phenol,
(RS)-4-[1-(4-phenyl-butyl)-pyrrolidin-3-yl-sulfanyl]-phenol,
(R)-4-[1-(4-phenyl-butyl)-pyrrolidin-3-yl-sulfanyl]-phenol,
(2R,3S) or (2S,3S)-4-[1-(2-hydroxy-4-phenyl-butyl)-pyrrolidin-3-yl-sulfanyl]-phenol,
(2S,3S) or (2S,3S)-4-[1-(2-hydroxy-4-phenyl-butyl)-pyrrolidin-3-yl-sulfanyl]-phenol,
(RS)-4-[1-(3-phenyl-propyl)-pyrrolidin-3-yl-sulfanyl]-phenol,
(3RS,3RS) and (3RS,3SR)-4-[1-(3-hydroxy-4-phenyl-butyl)-pyrrolidin-3-yl-sulfanyl]-phenol,
(2S,3R) or (2R,3R)-4-[1-(2-hydroxy-4-phenyl-butyl)-pyrrolidin-3-yl-sulfanyl]-phenol,
(2RS,3S)-4-[1-(2-fluoro-4-phenyl-butyl)-pyrrolidin-3-yl-sulfanyl]-phenol or
(2RS,3R)-4-[1-(2-fluoro-4-phenyl-butyl)-pyrrolidin-3-yl-sulfanyl]-phenol.

Compounds of the present invention, in which Ar¹ is phenyl, substituted by hydroxy, Q is —S(O)—, Ar² is phenyl and X is —CH₂— are further preferred, for example the following compound:

(3RS,S-oxide RS) and (3RS,S-oxide SR)-4-[1-(4-phenyl-butyl)-pyrrolidine-3-sulfinyl]-phenol,
(2R,3R,S-oxide R)-4-[1-(2-fluoro-4-phenyl-butyl)-pyrrolidine-3-sulfinyl]-phenol,
(2S,3S,S-oxide R)-4-[1-(2-fluoro-4-phenyl-butyl)-pyrrolidine-3-sulfinyl]-phenol,
(2R,3S,S-oxide R)-4-[1-(2-fluoro-4-phenyl-butyl)-pyrrolidine-3-sulfinyl]-phenol or
(3S,S-oxide S) or (3S,S-oxide R)-4-[1-(2,2-difluoro-4-phenyl-butyl)-pyrrolidine-3-sulfinyl]-phenol.

Further preferred are compounds, in which Ar¹ is phenyl, substituted by hydroxy, Q is —S(O)₂—, Ar² is indanyl or phenyl, optionally substituted by methyl and X is —CH₂— or —CH(OH)—, for example the following compounds:

(S)-4-[1-(4-phenyl-butyl)-pyrrolidine-3-sulfonyl]-phenol,
(RS)-4-[1-(4-phenyl-butyl)-pyrrolidine-3-sulfonyl]-phenol,
(2R,3S) and (2S,3S)-4-[1-(2-fluoro-4-phenyl-butyl)-pyrrolidine-3-sulfonyl]-phenol,(3RS,cis) and (3RS,trans)-4-[1-(3-benzyl-cyclobutyl)-pyrrolidine-3-sulfonyl]-phenol,
(3RS,cis)-4-[1-(4-phenyl-cyclohexyl)-pyrrolidine-3-sulfonyl]-phenol,
(3RS,4RS)-4-(4-hydroxy-benzenesulfonyl)-1-(4-phenyl-butyl)-pyrrolidin-3-ol,
(RS)-4-[1-(4-m-tolyl-butyl)-pyrrolidine-3-sulfonyl]-phenol,
(S)-4-[1-(3-phenyl-propyl)-pyrrolidine-3-sulfonyl]-phenol,
(R)-4-[1-(4-phenyl-butyl)-pyrrolidine-3-sulfonyl]-phenol,
(RS)-4-[1-(1-phenyl-piperidin-4-yl)-pyrrolidine-3-sulfonyl]-phenol or
(2R,3S) or (2S,3S)-4-[1-(2-hydroxy-4-phenyl-butyl)-pyrrolidine-3-sulfonyl]-phenol.

The afore-mentioned compounds of formula I can be manufactured in accordance with the invention by a) reacting a secondary amine of formula

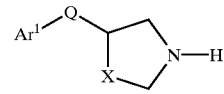

II with an aldehyde or ketone of formula

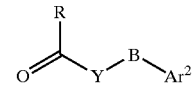

III to a compound of formula

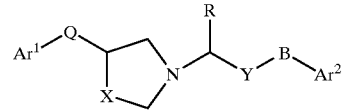

I-1 wherein Ar¹, Ar², Q, X, Y, R and B have the significance given above, or b) oxydizing a compound of formula

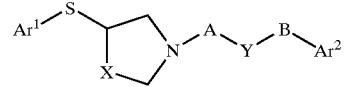

I-2 to a compound of formula

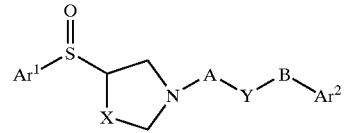

I-3 and/or to a compound of formula

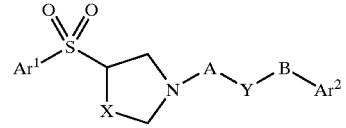

I-4 wherein Ar¹, Ar², X, A, Y and B have the significance given above, or c) reacting a secondary amine of formula

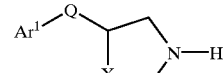

II with a compound of formula

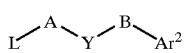
IV to give a compound of formula

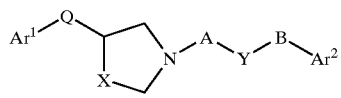
I wherein L is a leaving group, such as Cl, Br or p-toluenesulfonate and $Ar^1$, $Ar^2$, Q, X, A, Y and B have the significance given above, or d) reacting a secondary amine of formula

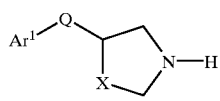
II to with a compound of formula

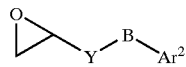
V to give a compound of formula

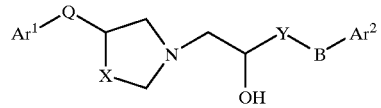
I-5 wherein $Ar^1$, $Ar^2$, Q, X, Y and B have the significance given above, or e) reacting a secondary amine of formula

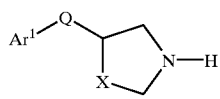
II with an aldehyde of formula

VI and with an alkyne of formula

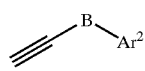
VII to give a compound of formula

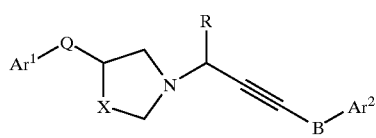
I-6 wherein $Ar^1$, $Ar^2$, Q, X, R and B have the significance given above, or f) reacting a compound of formula

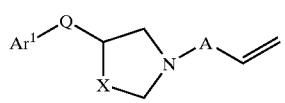
VIII with a compound of formula $Ar^2$hal to give a compound of formula

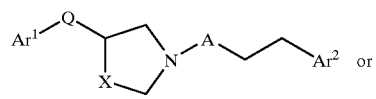
I-7 or

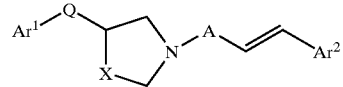
I-8 wherein $Ar^1$, $Ar^2$, Q, X and A have the significance given above, or g) cleaving off a O-protecting group of compounds of formula

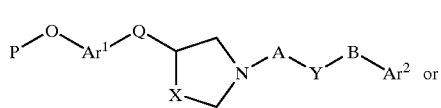
X or

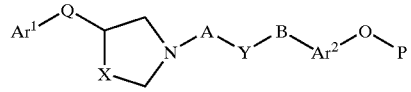
XI to obtain a compound of formula

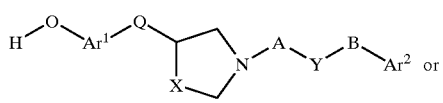
I-9 or

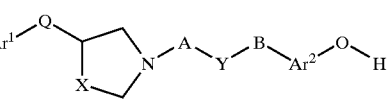
I-10 wherein $Ar^1$, $Ar^2$, Q, X, A, Y and B have the significance given above and P is a O-protecting, group, for example benzyl or a methoxymethyl group, or h) reducing a compound of formula

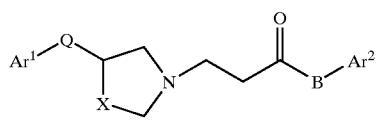

XII to a compound of formula

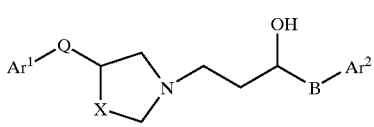

I-11 wherein Ar¹, Ar², Q, X and B have the significance given above; or i) reacting a compound of formula

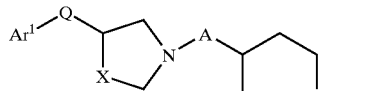

XIV-2 or

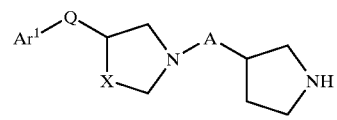

XIV-1 with a compound of formula

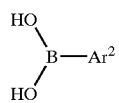

XV to obtain a compound of formula

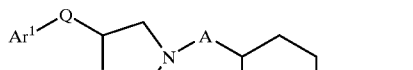

I-13 or

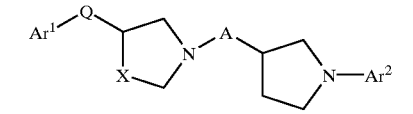

I-12 wherein Ar¹, Ar², Q, X, A and B have the significance given above; and if desired, modifying one or more substituents within the definitions given above, or if desired, converting the compound of formula I obtained into a pharmaceutically acceptable salt.

In the following the preparation of compounds of formula I are described in more detail:

Scheme 1

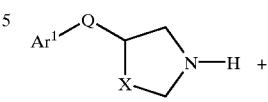

II

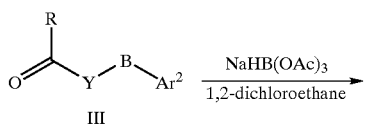

III

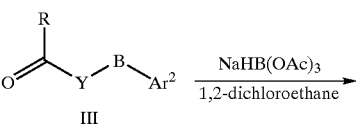

I-1 wherein Ar¹, Ar², Q, Y, R and B have the significance given above.

Compounds of formula I (A is —CHR—) can be prepared by reacting a secondary amine of formula II with an aldehyde or ketone of formula III in the presence of a reducing agent like NaHB(OAc)₃ in conventional manner.

Scheme 2

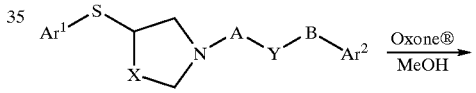

I-2

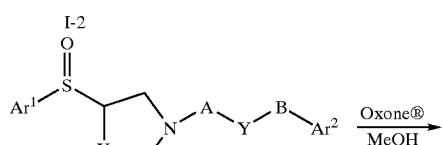

I-3

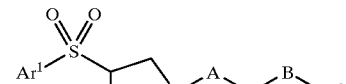

I-4 wherein Ar¹, Ar², X, A, Y, R and B have the significance given above. The compound of formula I-4 (Q is —SO₂—) can be prepared by oxidation of compounds of formula I-3 (Q is —SO—), which itself can be prepared by oxidation of compounds of formula I-2 (Q is —S—), using oxone® as oxidative agent. Oxone is a trade name for a stable oxidizing agent formed from a mixture consisting of 2KHSO5.KHSO4.KSO4. The oxidative agent and its use is described in Fieser and Fieser, Reagents for Organic Synthesis, vol. 1, (1967).

Scheme 3

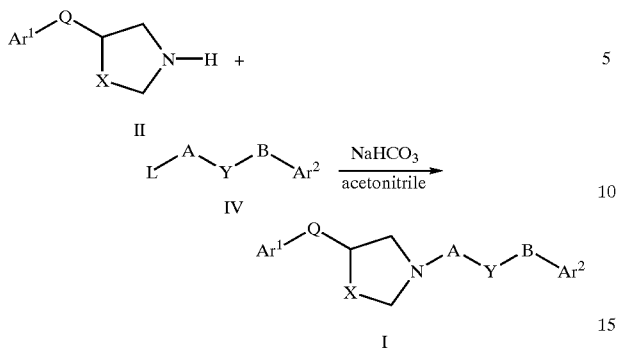

Compounds of formula I can be prepared by reacting an amine of formula II with an electrophile compound of formula IV, wherein L is a leaving group like Cl, Br or p-toluenesulfonate and the remaining substituents are described above.

Scheme 4

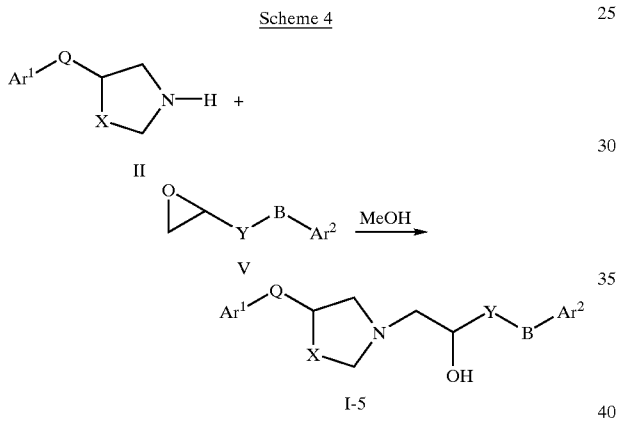

wherein $Ar^1$, $Ar^2$, Q, X, Y and B have the significance given above.

Compounds of formula I-5, wherein A is —CH$_2$—CH(OH)— can be prepared by reacting of an amine of formula II with an epoxide of formula V in conventional manner.

Scheme 5

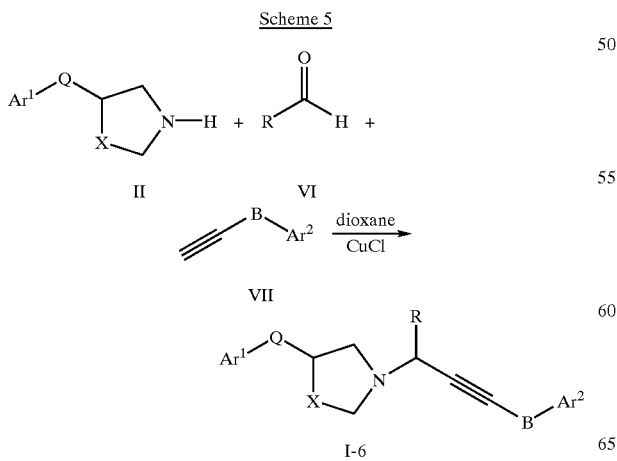

wherein $Ar^1$, $Ar^2$, Q, X, R and B have the significance given above.

Compounds of formula I-6, wherein A is —CHR— and Y is —C≡C— can be prepared under Mannich conditions by reacting an amine of compound of formula II with an aldehyde of formula VI and an alkyne of formula VII.

Scheme 6

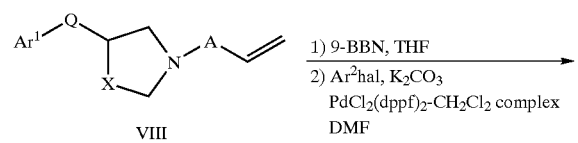

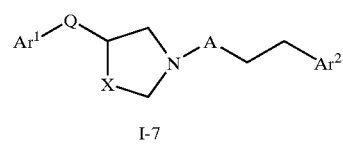

wherein $Ar^1$, $Ar^2$, Q, X and A have the significance given above.

Compounds of formula I-7, wherein Y is —CH$_2$ and B is —CH$_2$— can be prepared under Suzuki conditions by reacting an alkene of formula VIII with $Ar^2$hal, wherein hal is an, halogene like Br or I.

Scheme 7

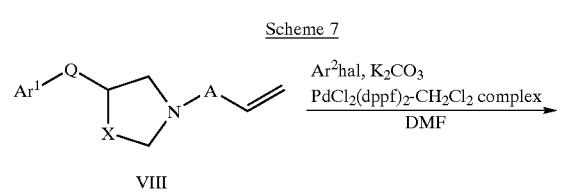

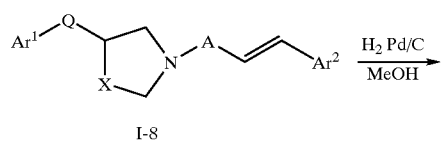

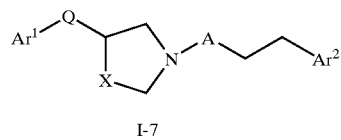

wherein $Ar^1$, $Ar^2$, Q, X and A have the significance given above.

Alternatively, compounds of formula I-7, wherein Y is —CH$_2$— and —B— is —CH$_2$— can be prepared in two steps under Heck conditions. Alkene compounds of formula VIII can react with $Ar^2$hal, wherein hal is an halogen like Br or I to provide an alkene derivative of formula I-8 which can be subsequently hydrogenated to obtain compounds of formula I-7.

Scheme 8

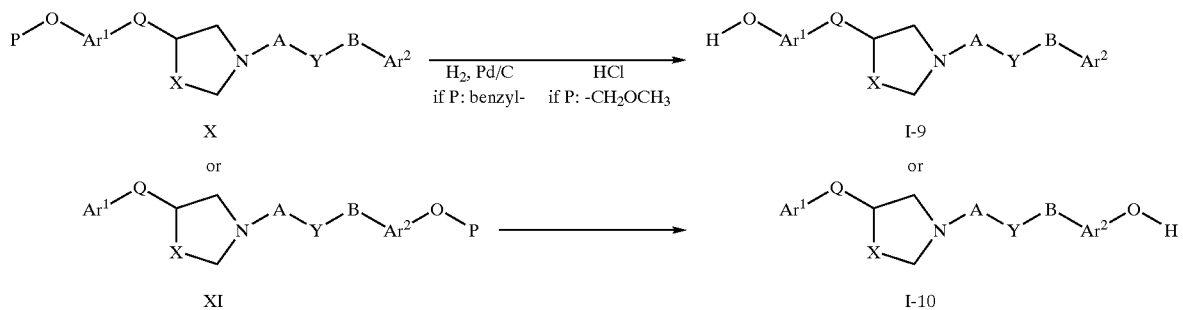

wherein Ar¹, Ar², Q, X, A, Y and B have the significance given above and P is a O-protecting group, which may be, for example benzyl or methoxymethyl.

Compounds of formula I-9 or of compounds of formula I-10 can be prepared by cleaving off an O-protecting group of compounds of formulas X or XI. $H_2$—Pd/C have been used to cleave a benzylether and acidic conditions have been used to cleave a methoxymethyl ether.

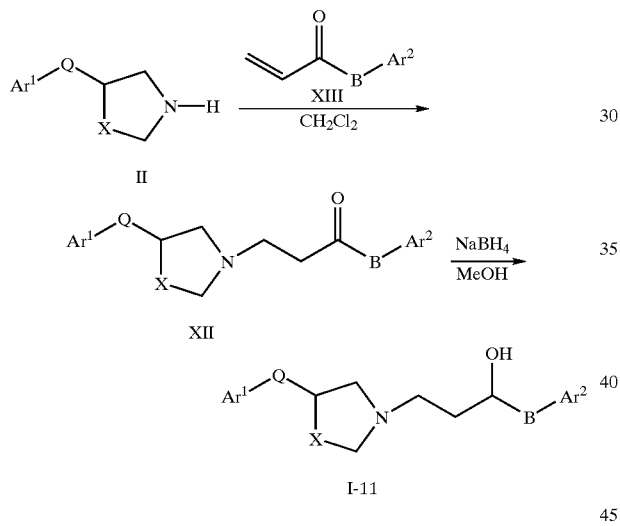

wherein Ar¹, Ar², Q, X and B have the significance given above.

Compounds of formula I-11, wherein A is —$CH_2$— and Y is —$CH_2CH(OH)$— can be prepared by reducing a ketone of formula XII, which itself can be prepared by reacting an amine of formula II with a Michael acceptor of formula XIII.

Scheme 10

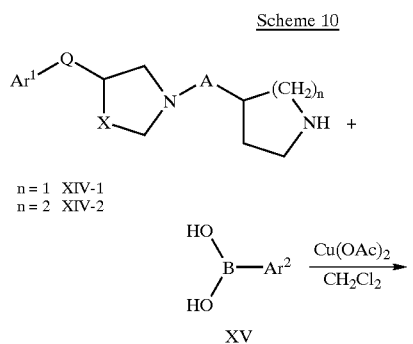

-continued

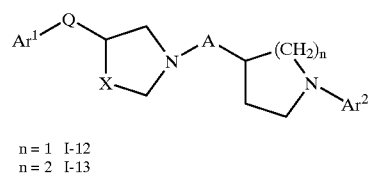

n = 1  I-12
n = 2  I-13 wherein Ar¹, Ar², Q, X, A and B have the significance given above.

Compounds of formula I-12 and I-13 can be prepared by reacting of an amine compound of formula XIV-1 or XIV-2 with boronic acid of formula XV.

Scheme 11

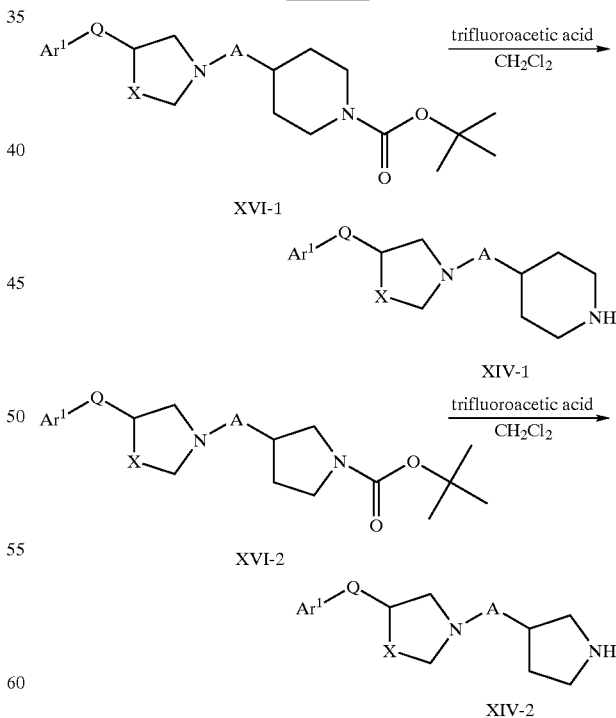

A compound of formula XIV-1 or of XIV-2 can be prepared by treating, the boc-protected amine compound of formula XVI-1 or XVI-2 with an acid, for example with trifluoroacetic acid.

Scheme 12

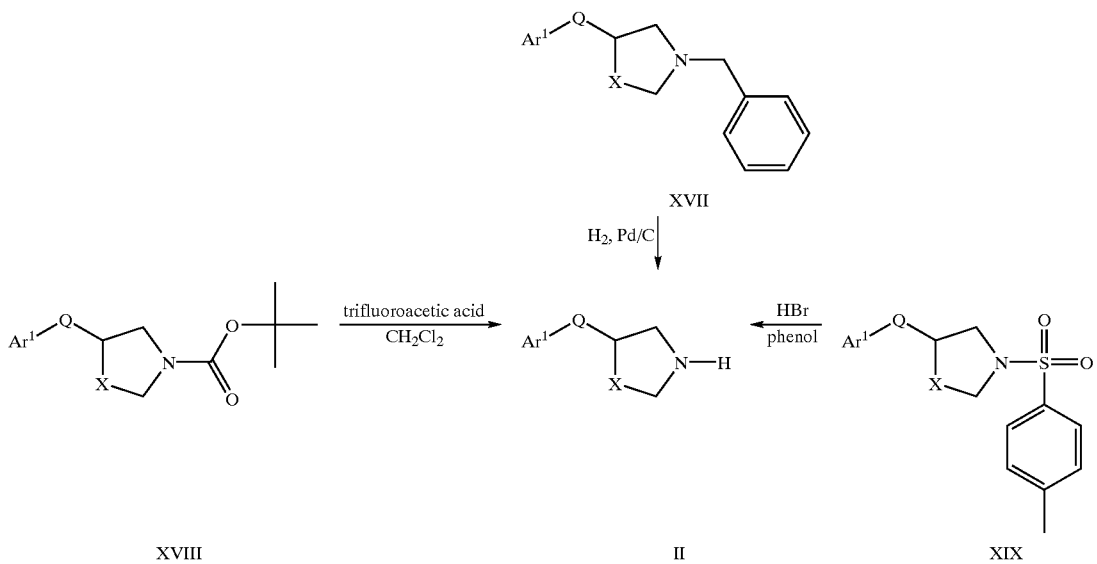

A compound of formula II can be prepared by hydrogenolysis of the benzylated amine of formula XVII, or by acidic hydrolysis of either the boc-protected amine compound of formula XVIII or the tosyl-protected amine compound of formula XIX.

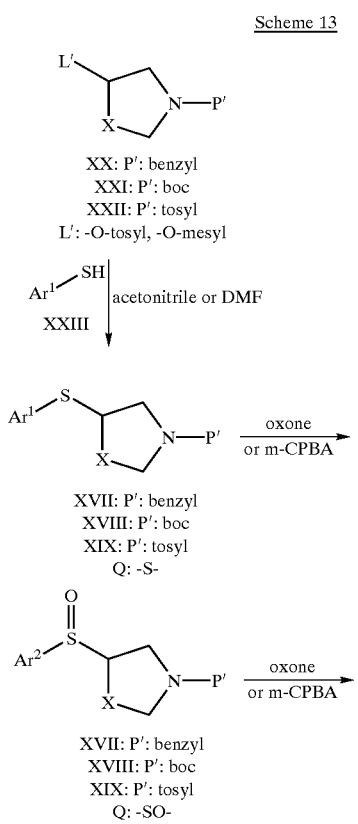

Compounds of formulas XVII, XVIII and XIX, wherein Q is —$SO_2$—, can be prepared by oxidation of compounds, respectively XVII, XVIII and XIX, wherein Q is —SO—, which themselves can be prepared by oxidation of compounds, respectively XVII, XVIII and XIX, wherein Q is —S—, using oxone or m-CPBA as oxidative agent.

Compounds of formulas XVII, XVIII and XIX, wherein Q is —S— can be prepared by reaction of a thiol of formula XXIII with respectively electrophiles of formulas XX, XXI and XXII, wherein L' is a leaving group, such as p-toluenesulfonate or mesylate.

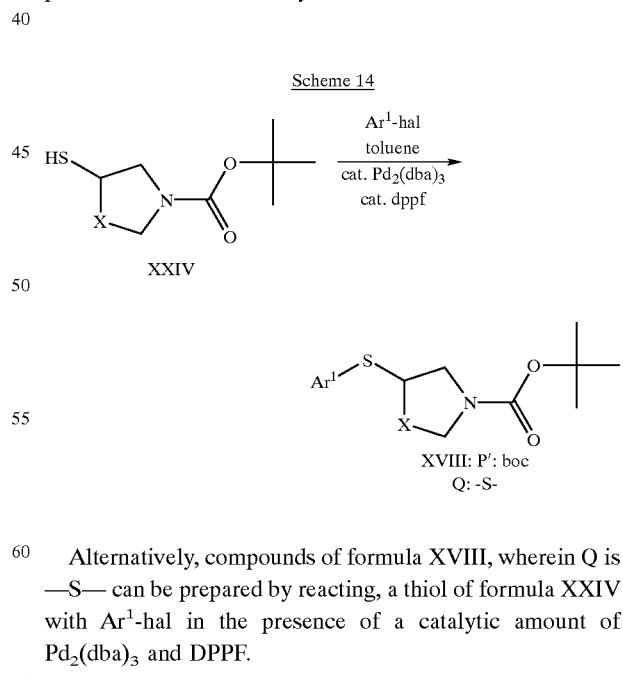

Alternatively, compounds of formula XVIII, wherein Q is —S— can be prepared by reacting, a thiol of formula XXIV with $Ar^1$-hal in the presence of a catalytic amount of $Pd_2(dba)_3$ and DPPF.

$Pd_2(dba)_3$ is tris(dibenzylideneacetone)dipalladium and dppf is 1,1'-bis(diphenylphosphino)ferrocene.

Scheme 15 Synthesis of monofluoro sulfoxides

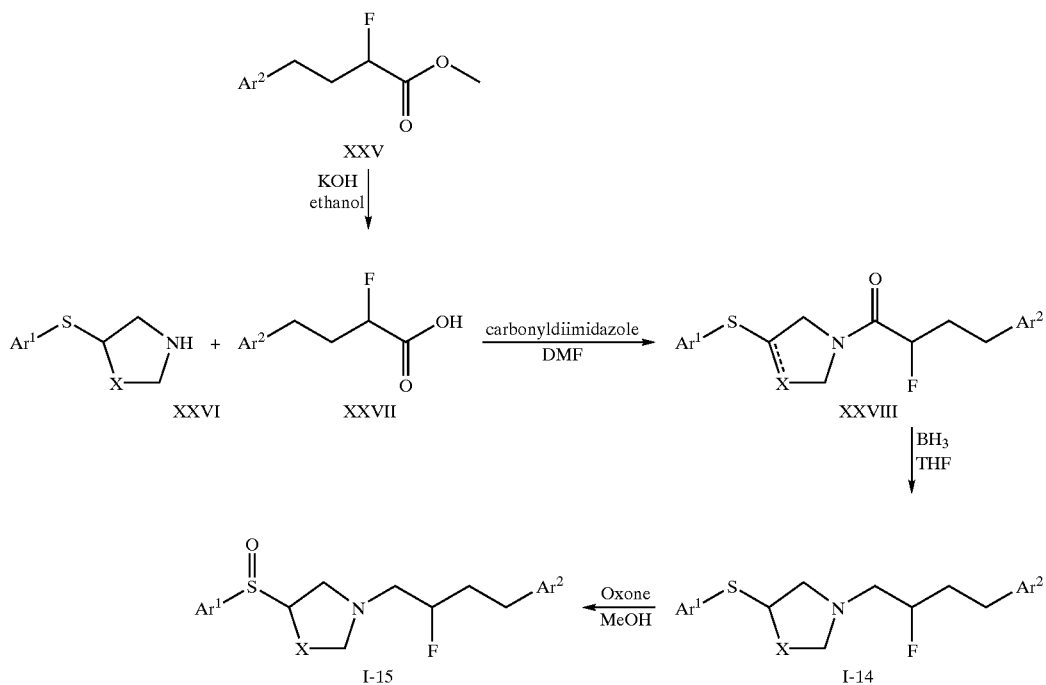

The monofluoro sulfoxides are obtained by oxidation of the corresponding sulfides with oxone. The sulfides are prepared by reduction of the amides with borane dimethylsulfide complex. The amides are accessible by coupling the racemic monofluoroacid with the R or S configured pyrrolidines in the presence of an activating agent like carbonyldiimidazole. The racemic acid is prepared by saponification of the corresponding racemic methyl ester. This methyl ester as well as the R or S configured pyrrolidines have been described in more detail in the working examples.

Scheme 16 Synthesis of difluoro sulfoxides:

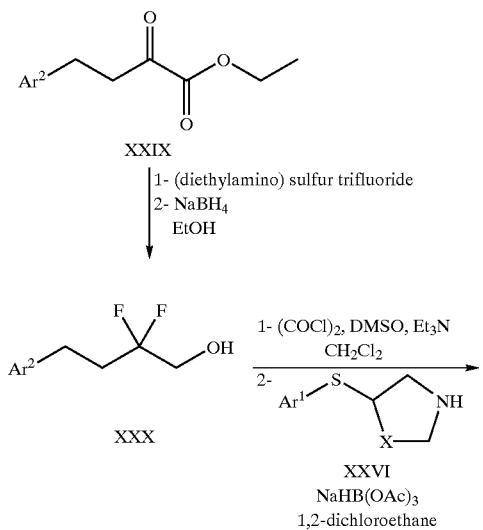

The difluoro sulfoxides are obtained by oxidation of the corresponding sulfides with oxone. The sulfides are prepared from the achiral difluoro alcohol after a Swern oxidation and reductive amination in the presence of an R or S configured pyrrolidine and sodium triacetoxyborohydride as reducing agent. The alcohol is obtained from the commercially available ethyl 2-oxo 4-phenylbutyrate after treatment with DAST ((diethylamino)sulfur trifluoride) and reduction with sodium borohydride.

The starting materials of formulas III, IV, V, VI, VII, XIII, XV, XX, XXI, XXII, XXIII, XXVI and XXIX are commercial products or can be prepared according to methods known per se.

Pharmaceutically acceptable salts can be manufactured according to methods which are known per se and familiar to any person skilled in the art. The acid addition salts of compounds of formula I are especially well suited for pharmaceutical use.

In schemes 1–10 and 15 and 16 are described processes for preparation of compounds of formula I, starting from known compounds, from commercial products or from compounds, which can be prepared in conventional manner. In schemes 11–14 are described processes for the preparation of intermediates.

The preparation of compounds of formula I are described in more detail in working examples 1–69.

As mentioned earlier, the compounds of formula I and their pharmaceutically usable acid addition salts possess valuable pharmacodynamic properties. They are NMDA-receptor subtype selective blockers, which have a key function in modulating neuronal activity and plasticity which makes them key players in mediating processes underlying development of CNS as well as learning and memory formation.

The compounds were investigated in accordance with the test given hereinafter.

Test Method

3H-Ro 25-6981 binding (Ro 25-6981 is [R—(R*, S*)]-a-(4-hydroxy-phenyl)-b-methyl-4-(phenyl-methyl)-1-piperidine propanol)

Male Füllinsdorf albino rats weighing between 150–200 g were used. Membranes were prepared by homogenization of the whole brain minus cerebellum and medulla oblongata with a Polytron (10,000 rpm, 30 seconds), in 25 volumes of a cold Tris-HCl 50 mM, EDTA 10 mM, pH 7.1 buffer. The homogenate was centrifuged at 48,000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

3H-Ro 25-6981 binding experiments were performed using a Tris-HCl 50 mM, pH 7.4 buffer. For displacement experiments 5 nM of 3H-Ro 25-6981 were used and non-specific binding was measured using 10 mM of tetrahydroisoquinoline and usually it accounts for 10% of the total. The incubation time was 2 hours at 4° C. and the assay was stopped by filtration on Whatman GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S.A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

The $IC_{50}$ ($\mu$M) of preferred compounds tested in accordance with the above mentioned methods are in the range of about 0.009–0.100.

Examples of some $IC_{50}$ values of preferred compounds are given in the table below:

| Example | $IC_{50}$ ($\mu$M) |
|---|---|
| 2 | 0.009 |
| 3 | 0.02 |
| 35 | 0.029 |
| 43 | 0.031 |
| 4 | 0.04 |
| 6 | 0.059 |
| 62 | 0.06 |
| 68 | 0.077 |
| 16 | 0.08 |

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives stabilizers, wetting or emulsifying agents, salts to change the osmotic pressure or to act as buffers. The pharmaceutical preparations can also contain other therapeutically active substances.

The dosage can vary within wide limits and will, of course, be fitted to the individual requirements in each particular case. In the case of oral administration the dosage lies in the range of about 0.1 mg per dosage to about 1000 mg per day of a compound of general formula I although the upper limit can also be exceeded when this is shown to be indicated.

The following examples illustrate the present invention in more detail. However, they are not intended to limit its scope in any manner. All temperatures are given in degrees Celsius.

EXAMPLE 1

(RS)-4-[1-(4-Phenyl-butyl)-pyrrolidine-3-sulfonyl]-phenol hydrochloride (RS)-4-(Pyrrolidine-3-sulfonyl)-phenol trifluoroacetic acid salt (0.22 g, 0.65 mmol), 4-phenyl-butyraldehyde (0.096 g, 0.65 mmol), triethylamine (0.090 ml., 0.65 mmol), and sodium triacetoxyborohydride (0.2 g, 0.97 mmol) were suspended in 1,2-dichloroethane (4 ml). After 3 hours stirring at room temperature, the reaction mixture was quenched with saturated $NaHCO_3$ (10 ml). The aqueous phase was extracted with $CH_2Cl_2$ (3 times). The combined organic phases were dried over $Na_2SO_4$, filtered and the solvent was evaporated. The residue was chromatographed over silica gel ($CH_2Cl_2$—MeOH, 19:1) to provide a white solid which was suspensed in MeOH. HCl-$Et_2O$ was added to provide (RS)-4-[1-(4-phenyl-butyl)-pyrrolidine-3-sulfonyl]-phenol hydrochloride (0.180 g, 70%) as a white solid, m.p. 121–124° C. and MS: m/e=360.3 (M+H$^+$).

4-Phenyl-butyraldehyde is a known compound and has been prepared as described in the following, reference: S. M. Moosavi; R. S. Beddoes; C. I. F. Watt; J. Chem. Soc. Perkin Trans. 2, 8, 1997, 1585–1596.

Following the general method of example 1 the compounds of example 2 to example 17 were prepared.

EXAMPLE 2

(S)-4-[1-(4-Phenyl-butyl)-pyrrolidin-3-yl-sulfanyl]-phenol

The title compound, MS: m/e=328.3 (M+H$^+$) and $[\alpha]_D^{20}$=−6.26° (c=0.61, chloroform) was prepared from (S)-4-(pyrrolidin-3-yl-sulfanyl)-phenol hydrobromide and 4-phenyl-butyraldehyde.

EXAMPLE 3

(R)-4-[1-(4-Phenyl-butyl)-pyrrolidin-3-yl-sulfanyl]-phenol

The title compound, MS: m/e=328.3 (M+H$^+$) and $[\alpha]_D^{20}$ +10.15° (c=0.56, chloroform) was prepared from (R)-4-(pyrrolidin-3-yl-sulfanyl)-phenol trifluoroacetic acid salt and 4-phenyl-butyraldehyde.

EXAMPLE 4

(3RS,cis) and (3RS,trans)-4-[1-(3-Benzyl-cyclobutyl)-pyrrolidine-3-sulfonyl]-phenol The title compound, MS: m/e=372.3 (M+H$^+$) was prepared from (RS)-4-(pyrrolidine-3-sulfonyl)-phenol trifluoroacetic acid salt and 3-benzyl-cyclobutanone.

EXAMPLE 5

(RS)-4-[1-(3-Phenyl-propyl)-pyrrolidin-3-yl-sulfanyl]-phenol hydrochloride

The title compound, MS: m/e=314.3 (M+H$^+$) was prepared from (RS)-4-(pyrrolidin-3-yl-sulfanyl)-phenol hydrobromide and 3-phenylpropionaldehyde.

EXAMPLE 6

(3RS,cis)-4-[1-(4-Phenyl-cyclohexyl)-pyrrolidine-3-sulfonyl]-phenol

The title compound, MS: m/e=386.3 (M+H$^+$) was prepared from (RS)-4-(pyrrolidine-3-sulfonyl)-phenol trifluoroacetic acid and 4-phenylcyclohexanone.

EXAMPLE 7

(3RS,trans)-4-[1-(4-Phenyl-cyclohexyl)-pyrrolidine-3-sulfonyl]-phenol

The title compound, MS: m/e=386.3 (M+H$^+$) was prepared from (RS)-4-(pyrrolidine-3-sulfonyl)-phenol trifluoroacetic acid and 4-phenylcyclohexanone.

EXAMPLE 8

(RS)-4-[1-(3-Phenyl-propyl)-piperidin-3-yl-sulfanyl]-phenol

The title compound, MS: m/e=328.3 (M+H$^+$) was prepared from (RS)-4-(piperidin-3-yl-sulfanyl)-phenol hydrobromide and 3-phenylpropionaldehyde.

EXAMPLE 9

(RS)-5-[1-(4-Phenyl-butyl)-pyrrolidine-3-sulfonyl]-1H-indazole

The title compound, MS: m/e=384.2(M+H$^+$) was prepared from (RS)-5-(pyrrolidine-3-sulfonyl)-1H-indazole trifluoroacetic acid and 4-phenyl-butyraldehyde.

EXAMPLE 10

(RS)-4-[1-(2-Benzyloxy-ethyl)-pyrrolidine-3-sulfonyl]-phenol

The title compound, MS: m/e=362.2 (M+H$^+$) was prepared from (RS)-4-(pyrrolidine-3-sulfonyl)-phenol trifluoroacetic acid salt and benzyloxyacetaldehyde.

EXAMPLE 11

4-[1-(4-Phenyl-butyl)-azetidine-3-sulfonyl]-phenol hydrochloride

The title compound, MS: m/e=346.3 (M+H$^+$) was prepared from 4-(azetidine-3-sulfonyl)-phenol and 4-phenyl-butyraldehyde.

EXAMPLE 12

(RS)-3-[1-(3-Phenyl-propyl)pyrrolidin-3-yl-sulfanyl]-phenol

The title compound, MS: m/e=314.3 (M+H$^+$) was prepared from (RS)-3-(pyrrolidin-3-yl-sulfanyl)-phenol hydrochloride and 3-phenylpropionaldehyde.

EXAMPLE 13

(RS)-6-[1-(4-Phenyl-butyl)-pyrrolidine-3-sulfonyl]-3H-benzooxazol-2-one

The title compound, MS: m/e=401.4 (M+H$^+$) was prepared from (RS)-6-(pyrrolidine-3-sulfonyl)-3H-benzooxazol-2-one trifluoroacetic acid and 4-phenyl-butyraldehyde.

EXAMPLE 14

(RS)-5-[1-(4-Phenyl-butyl)-pyrrolidine-3-sulfonyl]-1,3-dihydro-indol-2-one

The title compound, MS: m/e=399.4 (M+H$^+$) was prepared from (RS)-5-(pyrrolidine-3-sulfonyl)-1,3-dihydro-indol-2-one trifluoroacetic acid and 4-phenyl-butyraldehyde.

EXAMPLE 15

(RS)-4-[1-(4-Phenyl-butyl)-piperidin-3-yl-sulfanyl]-phenol

The title compound, MS: m/e=342.3 (M+H$^+$) was prepared from (RS)-4-(piperidin-3-yl-sulfanyl)-phenol hydrobromide and 4-phenyl-butyraldehyde.

EXAMPLE 16

(3RS,4RS)-4-(4-Hydroxy-benzenesulfonyl)-1-(4-phenyl-butyl)-pyrrolidin-3-ol

The title compound, MS: m/e=376.3 (M+H$^+$) was prepared from (3RS,4RS)-4-(4-hydroxy-benzenesulfonyl)-pyrrolidin-3-ol and 4-phenyl-butyraldehyde.

EXAMPLE 17

(RS)-4-[1-(4-Phenyl-butyl)-pyrrolidin-3-yl-sulfanyl]-phenol hydrochloride

The title compound, MS: m/e=328.2 (M+H$^+$) was prepared from (RS)-4-(pyrrolidin-3-yl-sulfanyl)-phenol hydrobromide and 4-phenyl-butyraldehyde.

EXAMPLE 18

(3RS,S-oxide RS) and (3RS,S-oxide SR)-4-[1-(4-Phenyl-butyl)-pyrrolidine-3-sulfinyl]-phenol hydrochloride (RS)-4-[1-(4-Phenyl-butyl)-pyrrolidin-3-yl-sulfanyl]-phenol (0.15 g, 0.46 mmol) was dissolved in MeOH (4 ml), cooled to 0° C. and treated with oxone (0.28 g, 0.46 mmol). After 1 hour stirring at 0° C., the reaction mixture was quenched with saturated NaHCO$_3$ (15 ml). The aqueous phase was extracted with CH$_2$Cl$_2$ (3 times). The combined organic phases were dried over Na$_2$SO$_4$, filtered and the solvent was evaporated. The residue was chromatographed over silica gel (ethyl acetate then ethyl acetate-MeOH, 95:5 then 9:1) to provide an oil which was suspensed in MeOH. HCl-Et$_2$O was added to provide (3RS,S-oxide RS) and (3RS,S-oxide SR)-4-[1-(4-phenyl-butyl)-pyrrolidine-3-sulfinyl]-phenol hydrochloride (0.04 g, 23%) as a foam, MS: m/e=344.2 (M+H$^+$).

Following the general method of example 18 the compounds of example 19 to example 30 were prepared.

EXAMPLE 19

(S)-4-[1-(4-Phenyl-butyl)-pyrrolidine-3-sulfonyl]-phenol

The title compound, MS: m/e=360.3 (M+H$^+$) and $[\alpha]_D^{20}$=+2.62° (c=0.534, chloroform) was prepared from (S)-4-[1-(4-phenyl-butyl)-pyrrolidin-3-yl-sulfanyl]-phenol.

EXAMPLE 20

(R)-4-[1-(4-Phenyl-butyl)-pyrrolidine-3-sulfonyl]-phenol hydrochloride

The title compound, MS: m/e=360.3 (M+H$^+$) was prepared from (R)-4-[1-(4-phenyl-butyl)-pyrrolidin-3-yl-sulfanyl]-phenol.

EXAMPLE 21

(RS)-4-[1-(3-Phenyl-propyl)-pyrrolidine-3-sulfonyl]-phenol hydrochloride

The title compound, MS: m/e=346.4 (M+H$^+$) was prepared from (RS)-4-[1-(3-phenyl-propyl)-pyrrolidin-3-yl-sulfanyl]-phenol.

EXAMPLE 22

(2R,3S) or (2S,3S)-4-[1-(2-Hydroxy-4-phenyl-butyl)-pyrrolidine-3-sulfonyl]-phenol The title compound, MS: m/e=376.4 (M+H$^+$) was prepared from (2R,3S) or (2S,3S)-4-[1-(2-hydroxy-4-phenyl-butyl)-pyrrolidin-3-yl-sulfanyl]-phenol.

EXAMPLE 23

(2S,3S) or (2R,3S)-4-[1-(2-Hydroxy-4-phenyl-butyl)-pyrrolidine-3-sulfonyl]-phenol The title compound, MS: m/e=376.4 (M+H$^+$) was prepared from (2S,3S) or (2R,3S)-4-[1-(2-hydroxy-4-phenyl-butyl)-pyrrolidin-3-yl-sulfanyl]-phenol.

EXAMPLE 24

(2R,3R) or (2S,3R)-4-[1-(2-Hydroxy-4-phenyl-butyl)-pyrrolidine-3-sulfonyl]-phenol The title compound, MS: m/e=376.3 (M+H$^+$) was prepared from (2R,3R) or (2S, 3R)-4-[1-(2-hydroxy-4-phenyl-butyl)-pyrrolidin-3-yl-sulfanyl]-phenol.

EXAMPLE 25

(2S,3R) or (2R,3R)-4-[1-(2-Hydroxy-4-phenyl-butyl)-pyrrolidine-3-sulfonyl]-phenol The title compound, MS: m/e=376.4 (M+H$^+$) was prepared from (2S,3R) or (2R,3R)-4-[1-(2-hydroxy-4-phenyl-butyl)-pyrrolidin-3-yl-sulfanyl]-phenol.

EXAMPLE 26

(3RS,S-oxide RS) and (3RS,S-oxide SR)-4-[1-(3-Phenyl-propyl)-piperidine-3-sulfinyl]phenol hydrochloride The title compound, MS: m/e=344.4 (M+H$^+$) was prepared from (RS)-4-[1-(3-phenyl-propyl)-piperidin-3-yl-sulfanyl]-phenol.

EXAMPLE 27

(RS)-4-[1-(3-Phenyl-propyl)-piperidine-3-sulfonyl]-phenol hydrochloride

The title compound, MS: m/e=360.3 (M+H$^+$) was prepared from (RS)-4-[1-(3-phenyl-propyl)-piperidin-3-yl-sulfanyl]-phenol.

EXAMPLE 28

(RS)-4-[1-(4-Phenyl-butyl)-piperidine-3-sulfonyl]-phenol hydrochloride

The title compound, MS: m/e=374.4 (M+H$^+$) was prepared from (RS)-4-[1-(4-phenyl-butyl)-piperidin-3-yl-sulfanyl]-phenol.

EXAMPLE 29

(3RS,S-oxide RS) and (3RS,S-oxide SR)-4-[1-(3-Phenyl-propyl)-pyrrolidine-3-sulfinyl]-phenol hydrochloride The title compound, MS: m/e=330.4 (M+H$^+$) was prepared from (RS)-4-[1-(3-phenyl-propyl)-pyrrolidin-3-yl-sulfanyl]-phenol.

EXAMPLE 30

(3RS,3RS) and (3RS,3SR)-4-[1-(3-Hydroxy-4-phenyl-butyl)-pyrrolidine-3-sulfonyl]-phenol The title compound, MS: m/e=376.4 (M+H$^+$) was prepared from (3RS,3RS) and (3RS,3SR)-4-[1-(3-hydroxy-4-phenyl-butyl)-pyrrolidin-3-yl-sulfanyl]-phenol.

EXAMPLE 31

(RS)-4-[1-(3-Phenoxy-propyl)-pyrrolidine-3-sulfonyl]-phenol(RS)-4-(pyrrolidine-3-sulfonyl)-phenol trifluoroacetic acid salt (0.2 g, 0.585 mmol), 3-phenoxypropylbromide (0.137 g, 0.64 mmol), and NaHCO$_3$ (0.1 g, 1.23 mmol) were suspended in acetonitrile (1.5 ml). After 24 hours stirring at 55° C., the reaction mixture was cooled to room temperature and quenched with saturated NaHCO$_3$. The aqueous phase was extracted with CH$_2$Cl$_2$ (3 times). The combined organic phases were washed with H$_2$O, dried over Na$_2$SO$_4$ and the solvent was evaporated. The residue was chromatographed over silica gel (CH$_2$Cl$_2$—MeOH, 19:1) to provide (RS)-4-[1-(3-phenoxy-propyl)-pyrrolidine-3-sulfonyl]-phenol (0.16 g, 75%) as a white foam, MS: m/e=362.2 (M+H$^+$).

Following the general method of example 31 the compounds of example 32 to example 38 were prepared.

EXAMPLE 32

(RS)-4-[1-(2-Indan-2-yl-ethyl)-pyrrolidine-3-sulfonyl]-phenol

The title compound, MS: m/e=372.3 (M+H$^+$) was prepared from (RS)-4-(pyrrolidine-3-sulfonyl)-phenol trifluo-

EXAMPLE 33

(RS)-2-{2-[3-(4-Hydroxy-benzenesulfonyl)-pyrrolidin-1-yl]-ethyl}-indan-2-ol hydrochloride The title compound, MS: m/e=388.2 (M+H$^+$) was prepared from (RS)-4-(pyrrolidine-3-sulfonyl)-phenol trifluoroacetic acid salt and toluene-4-sulfonic acid 2-(2-hydroxy-indan-2-yl)-ethyl ester.

EXAMPLE 34

(RS)-4-[1-(5-Phenyl-pentyl)-pyrrolidine-3-sulfonyl]-phenol

The title compound, MS: m/e=374.4 (M+H$^+$) was prepared from (RS)-4-(pyrrolidine-3-sulfonyl)-phenol trifluoroacetic acid salt and (5-bromo-pentyl)-benzene. (5-Bromopentyl)-benzene is a known compound and has been prepared as described in the following reference: J. Thomas; W. Marlow; J. Med. Chem.; 6; 1963; 107–111.

EXAMPLE 35

(2R,3S) and (2S,3S)-4-[1-(2-Fluoro-4-phenyl-butyl)-pyrrolidine-3-sulfonyl]-phenol The title compound, MS: m/e=378.3 (M+H$^+$) was prepared from (S)-4-(pyrrolidine-3-sulfonyl)-phenol trifluoroacetic acid salt and (RS)-toluene-4-sulfonic acid 2-fluoro-4-phenyl-butyl ester.

EXAMPLE 36

(2RS,3RS) and (2RS,3SR)-2-{2-[3-(4-Hydroxy-benzenesulfonyl)-pyrrolidin-1-yl]-ethyl}-1,2,3,4-tetrahydro-naphthalen-2-ol The title compound, MS: m/e=402.4 (M+H$^+$) was prepared from (RS)-4-(pyrrolidine-3-sulfonyl)-phenol trifluoroacetic acid salt and (RS)-2-(2-bromo-ethyl)-1,2,3,4-tetrahydro-naphthalen-2-ol.

EXAMPLE 37

(RS)-4-[1-(4-Phenyl-but-3-ynyl)-pyrrolidine-3-sulfonyl]-phenol

The title compound, MS: m/e=355.1 (M$^+$) was prepared from (RS)-4-(pyrrolidine-3-sulfonyl)-phenol trifluoroacetic acid salt and toluene-4-sulfonic acid 4-phenyl-but-3-ynyl ester.

EXAMPLE 38

(RS)-4-{1-[2-(1,3-Dihydro-isoindol-2-yl)-ethyl]-pyrrolidine-3-sulfonyl)-phenol hydrochloride The title compound, MS: m/e=373.3 (M+H$^+$) was prepared from (RS)-4-(pyrrolidine-3-sulfonyl)-phenol trifluoroacetic acid salt and 2-(2-chloro-ethyl)-2,3-dihydro-1H-isoindole. 2-(2-Chloro-ethyl)-2,3-dihydro-1H-isoindole is a known compound and has been prepared as described in the following reference: G. Shoeb; J. Pharm. Sci.; 51; 1962; 469–471.

EXAMPLE 39

(2R,3S) or (2S,3S)-4-[1-(2-Hydroxy-4-phenyl-butyl)-pyrrolidin-3-ylsulfanyl]phenol see Example 40.

EXAMPLE 40

(2S,3S) or (2R,3S)-4-[1-(2-Hydroxy-4-phenyl-butyl)-pyrrolidin-3-yl-sulfanyl]-phenol(S)-4-(pyrrolidin-3-yl-sulfanyl)-phenol hydrobromide (1 g, 3.6 mmol), (RS)-2-phenethyl-oxirane (0.8 g, 5.4 mmol) and triethylamine (0.76 ml, 5.4 mmol) were suspended in MeOH (20 ml). After 4 hours refluxing, the reaction mixture was cooled to room temperature and concentrated. The residue was chromatographed over silica gel (hexane-ethylacetate 1:1 then 1:4) to provide (2R,3S) or (2S,3S)-4-[1-(2-hydroxy-4-phenyl-butyl)-pyrrolidin-3-ylsulfanyl]-phenol (0.1 g, first fraction, 8%) as a colorless oil (Example 39) MS: m/e=344.4 (M+H$^+$) and (2S,3S) or (2R,3S)-4-[1-(2-hydroxy-4-phenyl-butyl)-pyrrolidin-3-ylsulfanyl]-phenol (0.13 g, second fraction, 10%) as a colorless oil (Example 40) MS: m/e=344.3 (M+H$^+$).(RS)-2-Phenethyl-oxirane is a known compound and has been prepared as described in the following reference: S. Levy; Bull. Soc. Chim. Fr.; 49; 1931; 1823–1826.

Following the general method of examples 39 and 40, compounds of example 41 to example 46 were prepared.

EXAMPLE 41

(2S,3R) or (2R,3R)-4-[1-(2-Hydroxy-4-phenyl-butyl)-pyrrolidin-3-yl-sulfanyl]-phenol The title compound, MS: m/e=344.4 (M+H$^+$) was prepared from (R)-4-(pyrrolidin-3-yl-sulfanyl)-phenol trifluoro-acetic acid and (RS)-2-phenethyl-oxirane.

EXAMPLE 42

(2R,3R) or (2S,3R)-4-[1-(2-Hydroxy-4-phenyl-butyl)-pyrrolidin-3-yl-sulfanyl]-phenol The title compound, MS: m/e=344.4 (M+H$^+$) was prepared from (R)-4-(pyrrolidin-3-yl-sulfanyl)-phenol trifluoro-acetic acid and (RS)-2-phenethyl-oxirane.

EXAMPLE 43

(2R,3S) and (2S,3S)-4-[1-(2-Hydroxy-2-indan-2-yl-ethyl)-pyrrolidine-3-sulfonyl]-phenol The title compound, MS: m/e=388.3 (M+H$^+$) was prepared from (S)-4-(pyrrolidine-3-sulfonyl)-phenol trifluoro-acetic acid and (RS)-2-indan-2-yl-oxirane.

EXAMPLE 44

(2RS,3RS) and (2RS,3SR)-4-[1-(2-Hydroxy-4-phenyl-butyl)-piperidin-3-yl-sulfanyl]-phenol The title compound, MS: m/e=358.2 (M+H$^+$) was prepared from (RS)-4-(piperidin-3-yl-sulfanyl)-phenol hydrobromide and (RS)-2-phenethyl-oxirane.

EXAMPLE 45

(3S,cis) or (3S,trans)-4-[1-(1-Hydroxy-3-phenyl-cyclobutylmethyl)-pyrrolidine-3-sulfonyl]-phenol The title compound, MS: m/e=388.3 (M+H$^+$) was prepared from (S)-4-(pyrrolidine-3-sulfonyl)-phenol trifluoro-acetic acid and cis or trans-5-phenyl-1-oxa-spiro[2.3]hexane.

EXAMPLE 46

(3S,trans) or (3S,cis)-4-[1-(1-Hydroxy-3-phenyl-cyclobutylmethyl)-pyrrolidine-3-sulfonyl]-phenol The title compound, MS: m/e=388.2 (M+H$^+$) was prepared from (S)-4-(pyrrolidine-3-sulfonyl)-phenol trifluoro-acetic acid and trans or cis-5-phenyl-1-oxa-spiro[2.3]hexane.

EXAMPLE 47

(RS)-4-[1-(4-Phenyl-but-2-ynyl)-pyrrolidine-3-sulfonyl]-phenol (RS)-4-(Pyrrolidine-3-sulfonyl)-phenol trifluoro-acetic acid (0.2 g, 0.59 mmol) and NaHCO$_3$ (74 mg, 0.88 mmol) were suspended in MeOH (2 ml). After 10 minutes, reaction mixture was concentrated. The residue was taken up in CHCl$_3$. The resulting solid was filtered and the filtrate was concentrated. The so-obtained foam was dissolved in dioxane (2 ml) and treated successively with paraformaldehyde (17.6 mg, 0.586 mmol), 3-phenyl-1-propyne (68 mg, 0.586 mmol) and CuCl (6.2 mg, 0.062 mmol). The reaction mixture was stirred at 100° C. for 0.75 hour then cooled to room temperature and concentrated. The residue was treated with saturated NaHCO$_3$. The aqueous phase was extracted with CH$_2$Cl$_2$ (3 times). The combined organic phases were dried over Na$_2$SO$_4$, filtered and the solvent was evaporated. The residue was chromatographed over silica gel (CH$_2$Cl$_2$—MeOH 19:1) to provide (RS)-4-[1-(4-phenyl-but-2-ynyl)-pyrrolidine-3-sulfonyl]-phenol (0.14 g, 69%) as an orange foam, MS: m/e=356.3 (M+H$^+$).

EXAMPLE 48

(RS)-4-[1-(4-m-Tolyl-butyl)-pyrrolidine-3-sulfonyl]-phenol

To a 0° C. solution of (RS)-4-(1-but-3-enyl-pyrrolidine-3-sulfonyl)-phenol (0.106 g, 0.378 mmol) in THF (0.5 ml), 9-BBN (1.66 ml, 0.74 ml, 0.5 M solution in THF) was added dropwise. The reaction mixture was allowed to warm up slowly to room temperature. After 4 hours stirring, the reaction mixture was treated successively with DMF (1.5 ml), 3-bromotoluene (0.046 ml, 0.377 mmol), PdCl$_2$(dppf)$_2$-dichloromethane complex (9.3 mg, 0.01 mmol), and K$_2$CO$_3$ (95 mg, 0.69 mmol). After 5 hours stirring at 60° C., the reaction mixture was cooled to room temperature, quenched with ethylacetate and H$_2$O. The aqueous phase was extracted with ethylacetate. The combined organic phases were washed with H$_2$O, dried over Na$_2$SO$_4$, filtered and concentrated. The residue was chromatographed over silica gel (CH$_2$Cl$_2$—MeOH, 98:2) to provide (RS)-4-[1-(4-m-tolyl-butyl)-pyrrolidine-3-sulfonyl]-phenol (66 mg, 47%) as a light yellow foam, MS: m/e=374.4 (M+H$^+$).

Following the general method of example 48 the compounds of example 49 to example 50 were prepared.

EXAMPLE 49

(RS)-4-{1-[4-(2-Methoxymethoxy-phenyl)-butyl]-pyrrolidine-3-sulfonyl}-phenol

The title compound, MS: m/e=420.3 (M+H$^+$) was prepared from (RS)-4-(1-but-3-enyl-pyrrolidine-3-sulfonyl)-phenol and 1-iodo-2-methoxymethoxy-benzene. 1-Iodo-2-methoxymethoxy-benzene is a known compound and has been prepared as described in the following reference: J. R. Labrosse; C. Poncet; P. Lhoste; D. Sinou; Tetrahedron, Asymmetry; 10; 6; 1999; 1069–1078.

EXAMPLE 50

(RS)-4-{1-[4-(3-Benzyloxy-phenyl)-butyl]-pyrrolidine-3-sulfonyl}-phenol

The title compound, MS: m/e 464.3 (M–H$^+$) was prepared from (RS)-4-(1-but-3-enyl-pyrrolidine-3-sulfonyl)-phenol and benzyl-(3-iodo-phenyl)-ether. Benzyl-(3-iodo-phenyl)-ether is a known compound and has been prepared as described in the following reference: W. Kipping; J. Chem. Soc.; 1957; 3246–3250.

EXAMPLE 51

(RS)-4-{1-[4-(3-Hydroxy-phenyl)-butyl]-pyrrolidine-3-sulfonyl}-phenol (RS)-4-{1-[4-(3-Benzyloxy-phenyl)-butyl]-pyrrolidine-3-sulfonyl}-phenol (88.4 mg, 0.2 mmol) and Pd/C (40 mg, 10% Pd on charcoal) in MeOH (5 ml) were refluxed for 2 hours under an atmospheric pressure of hydrogen. The reaction mixture was then cooled to room temperature, the catalyst was filtered and the filtrate was concentrated. The residue was chromatographed over silica gel (CH$_2$Cl$_2$—MeOH, 19:1) to provide (RS)-4-{1-[4-(3-hydroxy-phenyl)-butyl]-pyrrolidine-3-sulfonyl}-phenol (53 mg, 69%) as a light beige solid, MS: m/e=376.3 (M+H$^+$).

Following the general method of example 51 the compounds of example 52 to example 54 were prepared.

EXAMPLE 52

(RS)-4-{1-[4-(4-Hydroxy-phenyl)-butyl]-pyrrolidine-3-sulfonyl}-phenol

The title compound, MS: m/e=376.4 (M+H$^+$) was prepared from (RS)-4-{1-[4-(4-benzyloxy-phenyl)-butyl]-pyrrolidine-3-sulfonyl}-phenol.

EXAMPLE 53

(RS)-(4-Pyridin-3-yl-butyl)-pyrrolidine-3-sulfonyl]-phenol

The title compound, MS: m/e=361.2 (M+H$^+$) was prepared from (RS)-4-[1-(4-pyridin-3-yl-but-3-enyl)-pyrrolidine-3-sulfonyl]-phenol.

EXAMPLE 54

(3RS,4SR)-4-(4-Hydroxy-benzenesulfonyl)-1-(4-phenyl-butyl)-pyrrolidin-3-ol

The title compound, MS: m/e=376.4 (M+H$^+$) was prepared from (3RS,4SR)-4-(4-benzyloxy-benzenesulfonyl)-1-(4-phenyl-butyl)-pyrrolidin-3-ol.

EXAMPLE 55

(RS)-4-{1-[4-(2-Hydroxy-phenyl)-butyl]-pyrrolidine-3-sulfonyl}-phenol (RS)-4-{1-[4-(2-Methoxymethoxy-phenyl)-butyl]-pyrrolidine-3-sulfonyl}-phenol (34 mg, 0.08 mmol) in iPrOH (1 ml) was treated with HCl/Et$_2$O (1 ml). After 45 hours stirring at room temperature, the reaction mixture was quenched with saturated NaHCO$_3$. The aqueous phase was extracted with CH$_2$Cl$_2$. The combined organic phases were dried over Na$_2$SO$_4$, filtered and the solvent was evaporated. The residue was chromatographed over silica gel (CH$_2$Cl$_2$—MeOH, 19:1) to provide (RS)-4-{1-[4-(2-hydroxy-phenyl)- butyl]-pyrrolidine-3-sulfonyl}-3-phenol (17 mg, 56%) as a beige foam, MS: m/e=376.4 (M+H$^+$).

EXAMPLE 56

(3RS,3RS) and (3RS,3SR)-4-[1-(3-Hydroxy-4-phenyl-butyl)-pyrrolidin-3-yl-sulfanyl]-phenol (RS)-4-[3-(4-Hydroxy-phenylsulfanyl)-pyrrolidin-1-yl]-1-phenyl-butan-2-one (200 mg, 0.6 mmol) in MeOH (3 ml) was treated with NaBH$_4$ (33.2 mg, 0.9 mmol). After 15 minutes stirring at room temperature, the reaction mixture was acidified to pH 3 with 1N HCl then adjusted to pH 8 with saturated NaHCO$_3$. The aqueous phase was extracted with CH$_2$Cl$_2$. The combined organic phases were dried over Na$_2$SO$_4$, filtered and the solvent was evaporated. The residue was chromatographed over silica gel (ethylacetate) to provide (3RS, 3RS) and (3RS,3SR)-4-[1-(3-hydroxy-4-phenyl-butyl)-pyrrolidin-3-ylsulfanyl]-phenol (187 mg, 93%) as a white foam, MS: m/e=344.3 (M+H$^+$).

EXAMPLE 57

(RS)-4-[1-(1-Phenyl-piperidin-4-yl)-pyrrolidine-3-sulfonyl]-phenol (RS)-4-(1-Piperidin-4-yl-pyrrolidine-3-sulfonyl)-phenol trifluoroacetic acid (53.8 mg, 0.1 mmol), Et$_3$N (50.5 mg, 0.5 mmol), phenylboronic acid (36.6 mg, 0.3 mmol) and copper (II) acetate (36 mg, 0.2 mmol) were suspensed in CH$_2$Cl$_2$ (2 ml). After 3.5 hours stirring at room temperature, the reaction mixture was directly chromatographed over silica gel (CH$_2$Cl$_2$—MeOH 98:2 then 95:5) to provide (RS)-4-[1-(1-phenyl-piperidin-4-yl)-pyrrolidine-3-sulfonyl]-phenol (10 mg, 26%) as a white foam, MS: m/e=387.3 (M+H$^+$).

EXAMPLE 58

(2R,3R, S-oxide R)-4-[1-(2-Fluoro-4-phenyl-butyl)-pyrrolidine-3-sulfinyl]-phenol (2RS,3R)-4-[1-(2-Fluoro-4-phenyl-butyl)-pyrrolidin-3-ylsulfanyl]-phenol (0.56 g, 1.62 mmol) was dissolved in MeOH (50 ml), cooled to 0° C. and treated with oxone (0.5 g, 0.81 mmol). After 4 hours stirring at 0° C., reaction mixture was quenched with saturated NaHCO$_3$ (65 ml). Aqueous phase was extracted with CH$_2$Cl$_2$ (6 times). Combined organic phases were dried over Na$_2$SO$_4$ and the solvent was evaporated. The residue was chromatographed by MPLC over silica gel (CH$_2$Cl$_2$—MeOH, 99:1 then 98:2) then by preparative HPLC (EtOH-heptane, 08:92, detection at 254 nm) to provide (2R,3R, S-oxide R)-4-[1-(2-fluoro-4-phenyl-butyl)-pyrrolidine-3-sulfinyl]-phenol (30 mg, first fraction, 5%), MS: m/e=362.2 (M+H$^+$).

EXAMPLE 59

(2S,3R, S-oxide R)-4-[1-(2-Fluoro-4-phenyl-butyl)-pyrrolidine-3-sulfinyl]-phenol The title compound was prepared in accordance with example 58 to provide (2S,3R, S-oxide R)-4-[1-(2-fluoro-4-phenyl-butyl)-pyrrolidine-3-sulfinyl]-phenol (27 mg, second fraction, 4.7%), MS: m/e=362.2 (M+H$^+$).

EXAMPLE 60

(2RS,3R, S-oxide S)-4-[1-(2-Fluoro-4-phenyl-butyl)-pyrrolidine-3-sulfinyl]-phenol hydrochloride The title compound was prepared in accordance with example 58 to provide (2RS,3R, S-oxide S)-4-[1-(2-fluoro-4-phenyl-butyl)-pyrrolidine-3-sulfinyl]-phenol hydrochloride (100 mg, third fraction, 17%), MS: m/e=362.2 (M+H$^+$).

Following the general method of examples 58–60, the compounds of example 61 to 63 were prepared.

EXAMPLE 61

(2RS,3S,S-oxide S)-4-[1-(2-Fluoro-4-phenyl-butyl)-pyrrolidine-3-sulfinyl]-phenol hydrochloride The title compound, MS: m/e=362.2 (M+H$^+$) was prepared from (2RS,3S)-4-[1-(2-fluoro-4-phenyl-butyl)-pyrrolidin-3-ylsulfanyl]-phenol.

EXAMPLE 62

(2S,3S,S-oxide R)-4-[1-(2-Fluoro-4-phenyl-butyl)-pyrrolidine-3-sulfinyl]-phenol

The title compound, MS: m/e=362.2 (M+H$^+$) was prepared from (2RS,3S)-4-[1-(2-fluoro-4-phenyl-butyl)-pyrrolidin-3-ylsulfanyl]-phenol.

EXAMPLE 63

(2R,3S,S-oxide R)-4-[1-(2-Fluoro-4-phenyl-butyl)-pyrrolidine-3-sulfinyl]-phenol

The title compound, MS: m/e=362.2 (M+H$^+$) was prepared from (2RS,3S)-4-[1-(2-fluoro-4-phenyl-butyl)-pyrrolidin-3-ylsulfanyl]-phenol.

EXAMPLE 64

(3S,S-oxide R) or (3S,S-oxide S)-4-[1-(2,2-Difluoro-4-phenyl-butyl)-pyrrolidine-3-sulfinyl]-phenol (3S)-4-[1-(2,2-Difluoro-4-phenyl-butyl)-pyrrolidin-3-ylsulfanyl]-phenol (0.25 g, 0.688 mmol) was dissolved in MeOH (20 ml), cooled to 0° C. and treated with oxone (0.21 g, 0.34 mmol). After 4 hours stirring at 0° C., reaction mixture was quenched with saturated NaHCO$_3$ (65 ml). Aqueous phase was extracted with CH$_2$Cl$_2$ (3 times). Combined organic phases were dried over Na$_2$SO$_4$ and the solvent was evaporated. The residue was chromatographed by MPLC over silica gel (hexane-ethyl acetate, 98:2 to 50:50) to provide (3S,S-oxide R) or (3S, S-oxide S)-4-[1-(2,2-difluoro-4-phenyl-butyl)-pyrrolidine-3-sulfinyl]-phenol (140 mg, first fraction, 54%), MS: m/e=380.4 (M+H$^+$).

EXAMPLE 65

(3S,S-oxide S) or (3S,S-oxide R)-4-[1-(2,2-Difluoro-4-phenyl-butyl)-pyrrolidine-3-sulfinyl]-phenol The title compound was prepared in accordance with example 64 to provide (3S, S-oxide S) or (3S,S-oxide R)-4-[1-(2,2-difluoro-4-phenyl-butyl)-pyrrolidine-3-sulfinyl]-phenol (72 mg, second fraction, 28%), MS: m/e 380.4 (M+H$^+$). Following the general method of example 64 and 65, the compounds of example 66 and 67 were prepared.

EXAMPLE 66

(3R, S-oxide R) or (3R, S-oxide S)-4-[1-(2,2-Difluoro-4-phenyl-butyl)-pyrrolidine-3-sulfinyl]-phenol The title compound, MS: m/e=380.3 (M+H$^+$) was prepared from (3R)-4-[1-(2,2-difluoro-4-phenyl-butyl)-pyrrolidin-3-ylsulfanyl]-phenol.

EXAMPLE 67

(3R, S-oxide S) or (3R, S-oxide R)-4-[1-(2,2-Difluoro-4-phenyl-butyl)-]pyrrolidine-3-sulfinyl]-phenol The title compound, MS: m/e=380.3 (M+H$^+$) was prepared from (3R)-4-[1-(2,2-difluoro-4-phenyl-butyl)-pyrrolidin-3-ylsulfanyl]-phenol.

EXAMPLE 68

(2RS,3S)-4-[1-(2-Fluoro-4-phenyl-butyl)-pyrrolidin-3-ylsulfanyl]-phenol (2RS,3S)-2-Fluoro-1-[3-(4-hydroxy-phenylsulfanyl)-pyrrolidin-1-yl]-4-phenyl-butan-1-one (200 mg, 0.56 mmol) was dissolved in THF (4 ml). Borane-dimethylsulfide complex (170 µl, 1.67 mmol) was added. The mixture was refluxed for 7 hours and then cooled to 0° C. MeOH (0.7 ml) was added dropwise and the solvent was removed in vacuo. The residue was dissolved with THF (3.5 ml) and 5N HCl (1.1 ml) and was stirred at 60° C. for 12 hours. The solvent was removed in vacuo and the residue was taken up in saturated NaHCO$_3$ (3 ml). The aqueous layer was extracted with CH$_2$Cl$_2$ (3 times). The combined organic phases were dried over Na$_2$SO$_4$, filtered and the solvent was evaporated. The residue was chromatographed over silica gel (CH$_2$Cl—MeOH, 99:1) to provide (2RS,3S)-4-[1-(2-fluoro-4-phenyl-butyl)-pyrrolidin-3-ylsulfanyl]-phenol (134 mg, 70%) as colorless oil. MS: m/e 346.3 (M+H$^+$).

Following the general method of example 68 the compound of example 69 was prepared.

EXAMPLE 69

(2RS,3R)-4-[1-(2-Fluoro-4-phenyl-butyl)-pyrrolidin-3-ylsulfanyl]-phenol

The title compound, MS: m/e=346.3 (M+H$^+$) was prepared from (2RS,3R)-2-fluoro-1-[3-(4-hydroxy-phenylsulfanyl)-pyrrolidin-1-yl]-4-phenyl-butan-1-one.

Synthesis of Intermediates

EXAMPLE 70

(RS)-4-[3-(4-Hydroxy-phenylsulfanyl)-pyrrolidin-1-yl]-1-phenyl-butan-2-one (RS)-4-(Pyrrolidin-3-ylsulfanyl)-phenol hydrobromide (470 mg, 1.7 mmol), Et$_3$N (0.35 ml, 2.5 mmol) and 1-phenyl-3-butan-2-one (0.25 g, 1.7 mmol) were suspended in CH$_2$Cl$_2$ (10 ml). After stirring overnight at room temperature, the reaction mixture was concentrated and chromatographed over silica gel (hexane-ethylacetate 1:1 then ethylacetate) to provide (RS)-4-[3-(4-hydroxy-phenylsulfanyl)-pyrrolidin-1-yl]-1-phenyl-butan-2-one (90 mg, 16%) as a brown oil, MS: m/e 342.2 (M+H$^+$).

1-Phenyl-3-buten-2-one is a known compound and has been prepared as described in the following reference: E. Negishi; V. Bagheri; S. Chatterjee; M. Fen-Tair; J. A. Miller; T. A. Stoll; Tetrahedron Lett.; 24; 47; 1983; 5181–5184.

EXAMPLE 71

(RS)-4-(1-But-3-enyl-pyrrolidine-3-sulfonyl)-phenol

The title compound, MS: m/e=282.1 (M+H$^+$), has been prepared according to the procedure described for example 31 from (RS)-4-(pyrrolidine-3-sulfonyl)-phenol trifluoro-acetic acid salt and 4-bromo-butene.

EXAMPLE 72

(3RS,4SR)-4-(4-Benzyloxy-benzenesulfonyl)-1-(4-phenyl-butyl)-pyrrolidin-3-ol

The title compound, MS: m/e=466.3 (M+H$^+$), has been prepared according to the procedure described for example 1, from (3RS,4SR)-4-(4-benzyloxy-benzenesulfonyl)-pyrrolidin-3-ol trifluoro-acetic acid and 4-phenyl-butyraldehyde.

EXAMPLE 73

(RS)-4-[1-(4-Pyridin-3-yl-but-3-enyl)-pyrrolidine-3-sulfonyl]-phenol (RS)-4-(1-But-3-enyl-pyrrolidine-3-sulfonyl)-phenol (100 mg, 0.355 mmol), 3-bromopyridine (62 mg, 0.39 mmol), PdCl$_2$(dppf)$_2$-dichloromethane complex (9.3 mg, 0.01 mmol), and K$_2$CO$_3$ (95 mg, 0.69 mmol) were suspended in DMF (1.5 ml). After 5 hours stirring at 80° C., the reaction mixture was cooled to room temperature and concentrated. The residue was chromatographed over silica gel (CH$_2$Cl$_2$/MeOH 97:3 then 19/1) to provide (RS)-4-[1-(4-pyridin-3-yl-but-3-enyl)-pyrrolidine-3-sulfonyl]-phenol (100 mg, 78%) as a light orange foam, MS: m/e=359.2 (M+H$^+$).

EXAMPLE 74

(RS)-4-(Pyrrolidin-3-ylsulfanyl)-phenol hydrobromide (RS)-4-[1-(Toluene-4-sulfonyl)-pyrrolidin-3-ylsulfanyl]-phenol (1.9 g, 5.44 mmol) in phenol (5.1 g, 54.4 mmol) was treated with HBr (25 ml, 48%). After 4 hours stirring at 100° C., the reaction mixture was cooled to room temperature and quenched with H$_2$O and CH$_2$Cl$_2$. The aqueous phase was washed with CH$_2$Cl$_2$ and concentrated to provide (RS)-4-(pyrrolidin-3-ylsulfanyl)-phenol hydrobromide (1.13 g, 75%) as a brown oil, MS: m/e=196.2 (M+H$^+$). Following the general method of example 74, the compounds of example 75 to example 77 were prepared.

EXAMPLE 75

(S)-4-(Pyrrolidin-3-ylsulfanyl)-phenol hydrobromide

The title compound, MS: m/e=196.2 (M+H$^+$) and $[\alpha]_D^{20}$=−20.41°(c=1.02, MeOH) was prepared from (S)-4-[1-(toluene-4-sulfonyl)-pyrrolidin-3-ylsulfanyl]-phenol.

EXAMPLE 76

(RS)-4-(Piperidin-3-ylsulfanyl)-phenol hydrobromide

The title compound, MS: m/e=210.3 (M+H$^+$) was prepared from (RS)-4-[1-(toluene-4-sulfonyl)-piperidin-3-ylsulfanyl]-phenol.

EXAMPLE 77

(RS)-3-(Pyrrolidin-3-ylsulfanyl)-phenol hydrochloride

The title compound, MS: m/e=196.2 (M+H$^+$) was prepared from (RS)-3-(3-methoxy-phenylsulfanyl)-1-(toluene-4-sulfonyl)-pyrrolidine.

EXAMPLE 78

(R)-4-(Pyrrolidin-3-ylsulfanyl)-phenol trifluoroacetic acid (R)-3-(4-Hydroxy-phenylsulfanyl)-pyrrolidine-1-carboxylic acid tert-butyl ester (3.0 g, 10.2 mmol) in $CH_2Cl_2$ (36 ml) was treated with trifluoroacetic acid (7.8 ml, 0.1 mol). After 1 hour stirring at room temperature, the reaction mixture was concentrated to provide (R)-4-(pyrrolidin-3-yl-sulfanyl)-phenol trifluoroacetic acid (3.46 g) as an orange oil, MS: m/e=196.2 (M+H$^+$) and $[\alpha]_D^{20}$=+25.060 ° (c=1.2, MeOH).

Following the general method of example 78 the compounds of example 79 to example 86 were prepared.

EXAMPLE 79

(RS)-4-(Pyrrolidine-3-sulfonyl)-phenol trifluoro acetic acid

The title compound, MS: m/e=228.1 (M+H$^+$) was prepared from (RS)-3-(4-hydroxy-benzenesulfonyl)-pyrrolidine1-carboxyl acid tert-butyl ester.

EXAMPLE 80

(S)-4-(Pyrrolidine-3-sulfonyl)-phenol trifluoroacetic acid

The title compound, MS: m/e=228.1 (M+H$^+$) and $[\alpha]_D^{20}$=−3.45° (c=0.99, MeOH) was prepared from (S)-3-(4-hydroxy-benzenesulfonyl)-pyrrolidine-1-carboxylic acid tert-butyl ester.

EXAMPLE 81

(3RS,4RS)-4-(4-Hydroxy-benzenesulfonyl)-pyrrolidin-3-ol

The title compound, MS: m/e=244.2 (M+H$^+$) was prepared from 3-hydroxy-4-(4-hydroxy-benzenesulfonyl)-pyrrolidine1-carboxylic acid tert-butyl ester.

EXAMPLE 82

(3RS,4SR)-4-(4-Benzyloxy-benzenesulfonyl)-pyrrolidin-3-ol trifluoroacetic acid

The title compound, MS: m/e=334.2 (M+H$^+$) was prepared from (3RS,4SR)-3-(4-benzyloxy-benzenes-benzenesulfonyl)-4-hydroxy-pyrrolidine-1-carboxylic acid tert-butyl ester.

EXAMPLE 83

(RS)-5-(Pyrrolidine-3-sulfonyl)-1H-indazole trifluoroacetic acid

The title compound, MS: m/e=252.2 (M+H$^+$) was prepared from (RS)-5-(1-tert-butoxycarbonyl-pyrrolidine-3-sulfonyl)-indazole-1-carboxylic acid tert-butyl ester.

EXAMPLE 84

(RS)-5-(Pyrrolidine-3-sulfonyl)-1,3-dihydro-indol-2-one trifluoroacetic acid

The title compound, MS: m/e=267.0 (M+H$^+$) was prepared from (RS)-3-(2-oxo-2,3-dihydro-1H-indole-5-sulfonyl)-pyrrolidine-1-carboxylic acid tert-butyl ester.

EXAMPLE 85

(RS)-6-(Pyrrolidine-3-sulfonyl)-3H-benzooxazol-2-one trifluoroacetic acid

The title compound, MS: m/e=269.2 (M+H$^+$) was prepared from (RS)-3-(2-oxo-3-trityl-2,3-dihydro-benzooxazole-6-sulfonyl)-pyrrolidine1-carboxylic acid tert-butyl ester.

EXAMPLE 86

(RS)-4-(1-Piperidin-4-yl-pyrrolidine-3-sulfonyl)-phenol trifluoroacetic acid

The title compound, MS: m/e=311.3 (M+H$^+$) was prepared from (RS)-4-[3-(4-hydroxy-benzenesulfonyl)-pyrrolidin1-yl]-piperidine1-carboxylic acid tert-butyl ester.

EXAMPLE 87

(Azetidine-3-sulfonyl)-phenol

The title compound, MS: m/e=214.2 (M+H$^+$) was prepared from 4-(1-benzhydryl-azetidine-3-sulfonyl)-phenol following the procedure described for example 51.

EXAMPLE 88

(RS)-3-(4-Hydroxy-benzenesulfonyl)-pyrrolidine-1-carboxylic acid tert-butyl ester (RS)-3-(4-Hydroxy-phenylsulfanyl)-pyrrolidine-1-carboxylic acid tert-butyl ester (1.95 g, 6.6 mmol) was dissolved in MeOH (30 ml) and treated with oxone® (6.10 g, 9.9 mmol). After 3.5 hours stirring at room temperature, the reaction mixture was filtered and the filtrate was neutralized with saturated $NaHCO_3$. The aqueous phase was extracted with $CH_2Cl_2$ (3 times). The combined organic phases were dried over $Na_2SO_4$, filtered and the solvent was evaporated. The residue was chromatographed over silica gel (hexane-ethyl acetate 4:1 then 1:1) to provide (RS)-3-(4-hydroxy-benzenesulfonyl)-pyrrolidine-1-carboxylic acid tert-butyl ester (1.27 g, 58.8%) as a white foam, MS: m/e=328.2 (M+H$^+$).

Following the general method of example 88 the compounds of example 89 to example 91 were prepared

EXAMPLE 89

(S)-3-(4-Hydroxy-benzenesulfonyl)-pyrrolidine-1-carboxylic acid tert-butyl ester The title compound, MS: m/e=326.3 (M−H$^+$) and $[\alpha]_D^{20}$=−25.72° (c=1.07, chloroform) was prepared from (S)-3-(4-hydroxy-phenylsulfanyl)-pyrrolidine-1-carboxylic acid tert-butyl ester

EXAMPLE 90

(3RS,4RS)-3-Hydroxy-4-(4-hydroxy-benzenesulfonyl)-pyrrolidine-1-carboxylic acid tert-butyl ester The title compound, MS: m/e=344.4 (M−H$^+$) was prepared from (3RS,4RS)-3-hydroxy-4-(4-hydroxy-phenylsulfanyl)-pyrrolidine-1-carboxylic acid tert-butyl ester.

EXAMPLE 91

4-(1-Benzhydryl-azetidine-3-sulfonyl)-phenol

The title compound, MS: m/e=380.3 (M+H$^+$) was prepared from 4-(1-benzhydryl-azetidin-3-ylsulfanyl)-phenol.

EXAMPLE 92

(RS)-5-(1-tert-Butoxycarbonyl-pyrrolidine-3-sulfonyl)-indazole-1-carboxylic acid tert-butyl ester (RS)-5-(1-tert-Butoxycarbonyl-pyrrolidin-3-ylsulfanyl)-indazole-1-carboxylic acid tert-butyl ester (0.175 g, 0.41 mmol) was dissolved in $CH_2Cl_2$ (10 ml), cooled to 0° C. and treated with m-CPBA (0.26 g, 1.04 mmol, 70% of peracid). After 1 hour stirring at 0° C., the reaction mixture was quenched with saturated $NaHCO_3$. The organic phase was washed with saturated $NaHCO_3$, dried over $Na_2SO_4$, filtered and the solvent was evaporated. The residue was chromatographed over silica gel (hexane-ethyl acetate 9:1 then 4: 1 then 2:1) to provide (RS)-5-(1-tert-butoxycarbonyl-pyrrolidine-3-sulfonyl)-indazole1-carboxylic acid tert-butyl ester (0.127 g, 67.4%) as a white foam, MS: m/e=452.3 $(M+H^+)$.

Following the general method of example 92 the compounds of example 93 to example 94 were prepared.

EXAMPLE 93

(RS)-3-(2-Oxo-3-trityl-2,3-dihydro-benzooxazole-6-sulfonyl)-pyrrolidine-1-carboxylic acid tert-butyl ester The title compound, MS: m/e=628.1 $(M+NH_{4+})$ was prepared from (RS)-3-(2-oxo-3-trityl-2,3-dihydro-benzooxazol-6-yl-sulfanyl)-pyrrolidine-1-carboxylic acid tert-butyl.

EXAMPLE 94

(RS)-3-(2-Oxo-2,3-dihydro-1H-indole-5-sulfonyl)-pyrrolidine1-carboxylic acid tert-butyl ester The title compound, MS: m/e=384.2 $(M+NH_4^+)$ was prepared from (RS)-3-(2-oxo-2,3-dihydro-1 H-indol-5-yl-sulfanyl)-pyrrolidine-1-carboxylic acid tert-butyl ester.

EXAMPLE 95

(3RS,4SR)-3-(4-Benzyloxy-benzenesulfonyl)-4-hydroxy-pyrrolidine-1-carboxylic acid tert-butyl ester (RS)-3-(4-Benzyloxy-benzenesulfonyl)-4-oxo-pyrrolidine-1-carboxylic acid tert-butyl ester (13.4 mg, 0.031 mmol) was dissolved in MeOH (0.5 ml), cooled to 0° C. and treated with $NaBH_4$ (1.64 mg, 0.043 mmol). After 0.5 hour stirring at 0° C., the reaction mixture was acidified to pH 1 with 1N HCl. The aqueous phase was extracted with $CH_2Cl_2$. The combined organic phases were washed with $H_2O$, dried over $Na_2SO_4$, filtered and the solvent was evaporated to provide (3RS,4SR)-3-(4-benzyloxy-benzenesulfonyl)-4-hydroxy-pyrrolidine-1-carboxylic acid tert-butyl ester (12.3 mg, 92%) as a white solid, MS: m/e=434.4 $(M+H^+)$.

EXAMPLE 96

(RS)-3-(4-Benzyloxy-benzenesulfonyl)-4-oxo-pyrrolidine-1-carboxylic acid tert-butyl ester (3RS,4RS)-3-(4-Benzyloxy-benzenesulfonyl)-4-hydroxy-pyrrolidine-1-carboxylic acid tert-butyl ester (50 mg, 0.1 mmol) was dissolved in $CH_2Cl_2$ (2 ml) and treated successively with 4 Å molecular sieves (56 mg, powder) and pyridinium dichromate (56.4 mg, 0.15 mmol). After 3 hours stirring at room temperature, the reaction mixture was directly chromatographed over silica gel (hexane-ethyl acetate 4:1 then 1:1) to provide (RS)-3-(4-benzyloxy-benzenesulfonyl)-4-oxo-pyrrolidine-1-carboxylic acid tert-butyl ester (27 mg, 48%) as an oil, MS: m/e=374.2 (M-tbutyl).

EXAMPLE 97

(3RS,4RS)-3-(4-Benzyloxy-benzenesulfonyl)-4-hydroxy-pyrrolidine-1-carboxylic acid tert-butyl ester The title compound, MS: m/e=434.3 $(M+H^+)$ was prepared from (3RS,4RS)-3-(4-benzyloxy-phenyl-phenylsulfanyl)-4-hydroxy-pyrrolidine-1-carboxylic acid tert-butyl ester following the procedure described for example 88.

EXAMPLE 98

(3RS,4RS)-3-(4-Benzyloxy-phenylsulfanyl)-4-hydroxy-pyrrolidine-1-carboxylic acid tert-butyl ester (3RS,4RS)-3-Hydroxy-4-(4-hydroxy-phenylsulfanyl)-pyrrolidine-1-carboxylic acid tert-butyl ester (0.2 g, 0.6 mmol) was dissolved in acetone (5 ml), and treated with $K_2CO_3$ (0.1 g, 0.7 mmol). After 1 hour refluxing, the reaction mixture was cooled to room temperature and benzylbromide (0.084 ml, 0.7 mmol) was added. Reaction mixture was refluxed for an additional 3 hours then cooled to room temperature and quenched with $H_2O$. The aqueous phase was extracted with $CH_2Cl_2$, the combined organic phases were dried over $Na_2SO_4$, filtered and the solvent was evaporated. The residue was chromatographed over silica gel (hexane-ethyl acetate 2:1) to provide (3RS,4RS)-3-(4-benzyloxy-phenylsulfanyl)-4-hydroxy-pyrrolidine-1-carboxylic acid tert-butyl ester (0.208 g, 81%) as a yellow oil, MS: m/e=402.4 $(M+H^+)$.

EXAMPLE 99

(RS)-4-[3-(4-Hydroxy-benzenesulfonyl)-pyrrolidin-1-yl]-piperidine-1-carboxylic acid tert-butyl ester The title compound, MS: m/e=411.3 $(M+H^+)$ was prepared from (RS)-4-(pyrrolidine-3-sulfonyl)-phenol trifluoroacetic acid and 4-oxo-piperidine-1-carboxylic acid tert-butyl ester following the procedure described for example 1.

EXAMPLE 100

(RS)-3-(4-Hydroxy-phenylsulfanyl)-pyrrolidine-1-carboxylic acid tert-butyl ester (RS)-3-(Toluene-4-sulfonyloxy)-pyrrolidine-1-carboxylic acid tert-butyl ester (0.8 g, 2.34 mmol), 4-mercaptophenol (0.49 g, 3.88 mmol, 90%) and $Na_2CO_3$ (0.37 g, 3.51 mmol) were suspended in acetonitrile (10 ml). After 20 hours refluxing, reaction mixture was concentrated. The residue was taken up in $H_2O$ (15 ml) and extracted with $CH_2Cl_2$ (3 times). The combined organic phases were dried over $Na_2SO_4$, filtered and the solvent was evaporated. The residue was chromatographed over silica gel (hexane-ethylacetate 4:1 then 2:1) to provide (RS)-3-(4-hydroxy-phenylsulfanyl)-pyrrolidine-1-carboxylic acid tert-butyl ester (0.56 g, 81%) as a slightly yellow solid, MS: m/e= 296.4 $(M+H^+)$.(RS)-3-(Toluene-4-sulfonyloxy)-pyrrolidine-1-carboxylic acid tert-butyl ester is a known compound and has been prepared as described in WO 9734895.

Following the general method of example 100, the compounds of example 101 to example 108 were prepared.

EXAMPLE 101

(R)-3-(4-Hydroxy-phenylsulfanyl)-pyrrolidine-1-carboxylic acid tert-butyl ester The title compound, MS: m/e=295.1 ($M^+$) and $[\alpha]_D^{20}$=+20.09° (c=0.61, chloroform) was prepared from (S)-3-(toluene-4-sulfonyloxy)-pyrrolidine-1-carboxylic acid tert-butyl ester.

EXAMPLE 102

(S)-3-(4-Hydroxy-phenylsulfanyl)-pyrrolidine-1-carboxylic acid tert-butyl ester The title compound, MS: m/e=294.3 ($M-H^+$) and $[\alpha]_D^{20}$18.43° (c=0.52, chloroform) was prepared from (R)-3-(toluene-4-sulfonyloxy)-pyrrolidine-1-carboxylic acid tert-butyl ester. (R)-3-(Toluene-4-sulfonyloxy)-pyrrolidine-1-carboxylic acid tert-butyl ester is a known compound and has been prepared as described in the following reference: U. Nagel; H. G. Nedden; Chem. Ber., Recl.; 130; 3; 1997; 385–398.

EXAMPLE 103

(3RS, 4RS)-3-Hydroxy-4-(4-hydroxy-phenylsulfanyl)-pyrrolidine-1-carboxylic acid tert-butyl ester The title compound, MS: m/e=312.2 ($M+H^+$) was prepared from 6-oxa-3-aza-bicyclo[3.1.0]hexane-3-carboxylic acid tert-butyl ester.

6-Oxa-3-aza-bicyclo[3.1.0]hexane-3-carboxylic acid tert-butyl ester is a known compound and has been prepared as described in the following reference: C. Y. Hong; Y. K. Kim; Y. H. Lee; J. H. Kwak; Bioorg. Med. Chem. Lett.; 8; 3; 1998; 221–226.

EXAMPLE 104

4-(1-Benzhydryl-azetidin-3-ylsulfanyl)-phenol

The title compound, MS: m/e=348.4 ($M+H^+$) was prepared from methanesulfonic acid 1-benzhydryl-azetidin-3-yl ester by using DMF as solvent instead of acetonitrile. Methanesulfonic acid 1-benzhydryl-azetidin-3-yl ester is a known compound and has been prepared as described in the following reference: N. I. Carruthers; S. Wong; T. Chan; J. Chem. Res. Synop.; 9; 1996; 430–431.

EXAMPLE 105

(S)-4-[1-(Toluene-4-sulfonyl)-pyrrolidin-3-ylsulfanyl]-phenol

The title compound, MS: m/e=349.1 ($M^+$) and $[\alpha]_D^{20}$=−41.41° (c=1.10, chloroform) was prepared from (R)-toluene-4-sulfonic acid 1-(toluene-4-sulfonyl)-pyrrolidin-3-yl ester by using DMF as solvent instead of acetonitrile.

(R)-Toluene-4-sulfonic acid 1-(toluene-4-sulfonyl)-pyrrolidin-3-yl ester is a known compound and has been prepared as described in the following reference: A. Corruble; J. Y. Valnot; J. Maddaluno; P. Duhamel; J. Org. Chem.; Vol. 63; 23; 8274.

EXAMPLE 106

(RS)-4-[1-(Toluene-4-sulfonyl)-pyrrolidin-3-ylsulfanyl]-phenol

The title compound, MS: m/e=349.1 ($M^+$) was prepared from (RS)-toluene-4-sulfonic acid 1-(toluene-4-sulfonyl)-pyrrolidin-3-yl ester by using DMF as solvent instead of acetonitrile. (RS)-Toluene-4-sulfonic acid 1-(toluene-4-sulfonyl)-pyrrolidin-3-yl ester is a known compound and has been prepared as described in the following reference: J. R. Shanklin; C. P. Johnson; A. G. Proakis; R. J. Barrett; J. Med. Chem.; 1991; 34; 10; 3011–3022.

EXAMPLE 107

(RS)-4-[1-(Toluene-4-sulfonyl)-piperidin-3-ylsulfanyl]-phenol

The title compound, MS: m/e=363.0 ($M^+$) was prepared from (RS)-toluene-4-sulfonic acid 1-(toluene-4-sulfonyl)-piperidin-3-yl ester by using DMF as solvent instead of acetonitrile. (RS)-Toluene-4-sulfonic acid 1-(toluene-4-sulfonyl)-piperidin-3-yl ester is a known compound and has been prepared as described in the following reference: J. R. Shanklin; C. P. Johnson; A. G. Proakis; R. J. Barrett; J. Med. Chem.; 1991; 34; 10; 3011–3022.

EXAMPLE 108

(RS)-3-(3-Methoxy-phenylsulfanyl)-1-(toluene-4-sulfonyl)-pyrrolidine

The title compound, MS: m/e=363.1 ($M^+$) was prepared from (RS)-toluene-4-sulfonic acid 1-(toluene-4-sulfonyl)-pyrrolidin-3-yl ester and 3-methoxythiophenol and by using DMF as solvent instead of acetonitrile.

EXAMPLE 109

(S)-3-(Toluene-4-sulfonyloxy)-pyrrolidine-1-carboxylic acid tert-butyl ester To a 0° C. solution of (S)-3-hydroxy-pyrrolidine-1-carboxylic acid tert-butyl ester (8.5 g, 45.4 mmol), triethylamine (9.47 ml, 68.1 mmol) and dimethylaminopyridine (0.55 g, 4.5 mmol) in $CH_2Cl_2$ (150 ml) was added portionwise p-toluenesulfonyl chloride (9.52 g, 49.9 mmol). After 48 hours stirring at room temperature, reaction mixture was acidified to pH 1 with 1N HCl and aqueous phase was extracted with $CH_2Cl_2$. Combined organic phases were washed with 1N HCl and $H_2O$, dried over $Na_2SO_4$ and concentrated. The residue was chromatographed over silica gel (hexane-ethylacetate 9:1 then 8:2 then 1:1) to provide (S)-3-(toluene-4-sulfonyloxy)-pyrrolidine-1-carboxylic acid tert-butyl ester (13.1 g, 87%) as a slightly yellow oil, MS: m/e=268.1 (M-OtBu) and $[\alpha]_D^{20}$=+17.55° (c=3.33, diethylether).

(S)-3-Hydroxy-pyrrolidine-1-carboxylic acid tert-butyl ester is a known compound and has been prepared as described in the following reference: U. Nagel; H. G. Nedden; Chem. Ber.; Recl.; 130; 3; 1997; 385–398.

Following the general method of example 109, the compounds of example 110 to example 111 were prepared.

EXAMPLE 110

(RS)-Toluene-4-sulfonic acid 2-fluoro-4-phenyl-butyl ester

The title compound, MS: m/e=322.1 ($M^+$) was prepared from (RS)-2-fluoro-4-phenyl-butan-1-ol.

EXAMPLE 111

Toluene-4-sulfonic acid 2-(2-hydroxy-indan-2-yl)-ethyl ester

The title compound, MS: m/e=355.2 ($M+Na^+$) was prepared from 2-(2-hydroxy-ethyl)-indan-2-ol.

EXAMPLE 112

(RS)-2-(2-Bromo-ethyl)1,2,3,4-tetrahydro-naphthalen-2-ol

To a 0° C. solution of triphenylphosphine (1.03 g, 3.93 mmol), in $CH_2Cl_2$ (15 ml) was added slowly a solution of bromine (0.192 ml, 3.74 mmol) in $CH_2Cl_2$. After 1 hour stirring at room temperature, the reaction mixture was cooled to 0° C. and treated slowly with a solution of (RS)-2-(2-hydroxy-ethyl)-1,2,3,4-tetrahydro-naphthalen-2-ol (0.72 g, 3.74 mmol) in $CH_2Cl_2$ (15 ml). After 1.5 hour stirring at room temperature, the reaction mixture was again cooled to 0° C., treated slowly with triethylamine (0.52 ml, 3.74 mmol), washed successively with $H_2O$ and brine, dried over $Na_2SO_4$, filtered and concentrated. The residue was chromatographed over silica gel (hexane-ethylacetate 9:1) to provide (RS)-2-(2-bromo-ethyl)-1,2,3,4-tetrahydro-naphthalen-2-ol (0.58 g, 61%) as a colorless oil, MS: m/e= 255.1 (M).

EXAMPLE 113

(RS)-2-Fluoro-4-phenyl-butan1-ol

To a 0° C. suspension of $LiAlH_4$ (0.4 g, 10.6 mmol) in dry THF (5 ml) was added dropwise a solution of (RS)-2-fluoro-4-phenyl-butyric acid methyl ester (1 g, 5.3 mmol) in dry THF (10 ml). After 1 hour stirring at 0° C., the reaction mixture was quenched successively with $H_2O$ (0.4 ml), 5N NaOH (0.4 ml) and again $H_2O$ (1.2 ml). The resulting solid was filtered and the filtrate was concentrated to provide (RS)-2-fluoro-4-phenyl-butan-1-ol (0.89 g, 99%) as a colorless oil, MS: m/e=168.1 ($M^+$).

Following the general method of example 113, the compounds of example 114 to example 115 were prepared.

EXAMPLE 114

2-(2-Hydroxy-ethyl)-indan-2-ol

The title compound, MS: m/e=178.1 ($M^+$) was prepared from (2-hydroxy-indan-2-yl)-acetic acid methyl ester.

(2-Hydroxy-indan-2-yl)-acetic acid methyl ester is a known compound and has been prepared as described in the following reference: H. R. Veen; H. Cerfontain; Can. J. Chem.; 62; 1984; 2202–2205.

EXAMPLE 115

(RS)-2-(2-Hydroxy-ethyl)-1,2,3,4-tetrahydro-naphthalen-2-ol

The title compound, MS: m/e=192.3 ($M^+$) was prepared from (RS)-(2-hydroxy-1,2,3,4-tetrahydro-naphthalen-2-yl)-acetic acid methyl ester.

(RS)-(2-Hydroxy-1,2,3,4-tetrahydro-naphthalen-2-yl)-acetic acid methyl ester is a known compound and has been prepared as described in the following reference: H. R. Veen; H. Cerfontain; Can. J. Chem.; 62; 1984; 2202–2205.

EXAMPLE 116

(RS)-5-(1-tert-Butoxycarbonyl-pyrrolidin-3-yl-sulfanyl)-indazole1-carboxylic acid tert-butyl ester To a room temperature solution of (RS)-3-(1H-indazol-5-ylsulfanyl)-pyrrolidine-1-carboxylic acid tert-butyl ester (0.2 g, 0.61 mmol), and dimethylaminopyridine (7.4 mg, 0.06 mmol) in $CH_2Cl_2$ (3 ml) was added slowly a solution of di-tert-butyl dicarbonate (0.13 g, 0.61 mmol) in $CH_2Cl_2$. After 30 minutes stirring at room temperature, the reaction mixture was washed with $H_2O$, dried over $Na_2SO_4$, filtered and concentrated. The residue was chromatographed over silica gel (hexane-ethylacetate 9:1 then 8:2) to provide (RS)-5-(1-tert-butoxycarbonyl-pyrrolidin-3-ylsulfanyl)-indazole-1-carboxylic acid tert-butyl ester (0.19 g, 74%) as a yellow oil, MS: m/e=420.4 ($M+H^+$).

EXAMPLE 117

(RS)-3-(2-Oxo-3-trityl-2,3-dihydro-benzooxazol-6-yl-sulfanyl)-pyrrolidine-1-carboxylic acid tert-butyl ester Tris(dibenzylideneacetone)dipalladium chloroform complex (14 mg, 13.5 □mol) and 1,1'-bis(diphenylphosphino)ferrocene (30 mg, 54.1 □mol) in degassed and dry toluene (2 ml) were stirred at room temperature until the solution turned orange (15 minutes). 6-Bromo-3-trityl -3H-benzooxazol-2-one (0.2 g, 0.44 mmol), $Cs_2CO_3$ (0.22 g, 0.68 mmol) and (RS) -3-mercapto-pyrrolidine-1-carboxylic acid tert-butyl ester (0.1 g, 0.49 mmol) in toluene (0.5 ml) were successively added. After 4 hours stirring at 100° C., the reaction mixture was cooled to room temperature and concentrated. The residue was chromatographed over silica gel (hexane-ethylacetate 9:1 then 1:1) to provide (RS)-3-(2-oxo-3-trityl-2,3-dihydro-benzooxazol-6-yl-sulfanyl)-pyrrolidine-1-carboxylic acid tert-butyl ester (0.19 g 7 77%) as a white foam, MS: m/e=596.1 ($M+NH_4^+$).

Following the general method of example 117 the compounds of example 118 to example 119 were prepared.

EXAMPLE 118

(RS)-3-(1H-Indazol-5-yl-sulfanyl)-pyrrolidine-1-carboxylic acid tert-butyl ester The title compound, MS: m/e=319.1 ($M^+$) was prepared from 5-iodo-1H-indazole. 5-Iodo1H-indazole is a known compound and has been prepared as described in the following reference: L. Auwers; Chem. Ber.; 55; 1922; 1172.

EXAMPLE 119

(RS)-3-(2-Oxo-2,3-dihydro-1H-indol-5-yl-sulfanyl)-pyrrolidine-1-carboxylic acid tert-butyl ester The title compound, MS: m/e=334.4 ($M^+$) was prepared from 5-iodo-1,3-dihydro-indol -2-one.

EXAMPLE 120

5-Iodo1,3-dihydro-indol-2-one

A solution of 2-indolinone (2.66 g, 20 mmol) in acetic acid (20 ml) was stirred at room temperature in the presence of N-iodosuccinimide (5.4 g, 24 mmol) for 2 hours. $H_2O$ (150 ml) was then added. The precipitate was filtered, washed with $H_2O$, and dried. The resulting solid was refluxed in ethyl acetate (50 ml), cooled to 0° C., filtered, washed with ethylacetate and ether and dried to provide 5-iodo-1,3-dihydro-indol-2-one (3.62 g. 70%) as a beige solid, m.p. 190–192° C. and MS: m/e=259 ($M^+$).

EXAMPLE 121

6-Bromo-3-trityl-3H-benzooxazol-2-one

6-Bromo-3H-benzooxazol-2-one (0.165 g, 0.77 mmol) was added portionwise into a 0° C. suspension of NaH (44.8 mg, 1mmol, 55%) in dry DMF (4 ml). After 1 hour stirring at room temperature, a solution of triphenylmethylchloride (0.24 g, 0.85 mmol) in DMF (0.5 ml) was added. The reaction mixture was stirred 1 hour at room temperature then quenched with $H_2O$ (15 ml). The aqueous phase was extracted with ethyl acetate, the combined organic phases were washed with $H_2O$ and brine, dried over $Na_2SO_4$ and concentrated to provide 6-bromo -3-trityl-3H-benzooxazol-2-one (0.27 g, 77 %) as a beige solid, MS: m/e=457.1 (M+H$^+$).

6-Bromo-3H-benzooxazol-2-one is a known compound and has been prepared as described in the following reference: H. Gershon; D. D. Clarke; M. Gershon; Monatsh. Chem.; 1993; 124; 4; 367–379.

EXAMPLE 122

(RS)-2-Fluoro-4-phenyl-butyric acid methyl ester nBuLi (13.8 ml, 22 mmol, 1.6 M in hexane) was added dropwise into a 0° C. solution of diisopropylamine (3.39 ml,24 mmol) in THF (34 ml). The reaction mixture was stirred at 0° C. for 15 minutes then cooled to −75 ° C. and treated slowly with a solution of methyl 4-phenylbutyrate (3.56 g, 20 mmol) in THF (10 ml). After 30 minutes stirring at −75° C., trimethylchlorosilane ( 5.06 ml, 40 mmol) was added dropwise and the reaction mixture was allowed to warm up to room temperature. After 30 minutes, reaction mixture was concentrated, the residue was taken up in $CH_2Cl_2$ (100 ml), the resulting precipitate was filtered, filtrate was cooled to 13° C. and subsequently treated slowly with a solution of N-fluorodibenzenesulfonimide (6.3 g, 20 mmol) in $CH_2Cl_2$ (50 ml). After 3 hours stirring at room temperature, the reaction mixture was washed with $H_2O$ (2 times). The aqueous phase was extracted with $CH_2Cl_2$, the combined organic phases were dried over $Na_2SO_4$ and concentrated. The residue was chromatographed over silica gel (hexane-ethylacetate 99:1 then 98:2) to provide (RS)-2-fluoro-4-phenyl-butyric acid methyl ester (2.47 g, 63%) as a colorless oil, MS: m/e=196.1 (M$^+$).

Methyl 4-phenylbutyrate is a known compound and has been prepared as described in the following reference: M. V. Bhatt; M. Ravindranathan; V. Somayaji; G. V. Rao; J. Org. Chem; 49; 17; 1984; 3170–3173.

EXAMPLE 123

(RS)-3-Mercapto-pyrrolidine-1-carboxylic acid tert-butyl ester

To a 0° C. solution of (RS)-3-acetylsulfanyl-pyrrolidine-1-carboxylic acid tert-butyl ester (1.4 g, 5.07 mmol) in MeOH (15 ml) was added dropwise a suspension of sodium methoxide (0.61 g, 11.3 mmol) in MeOH. After 6 hours stirring at room temperature, the reaction mixture was neutralized with 1N HCl and MeOH was partially evaporated. $H_2O$ and ethylacetate were added. The aqueous phase was extracted with ethylacetate, the combined organic phases were washed with brine, dried over $Na_2SO_4$, filtered and concentrated to provide (RS)-3-mercapto-pyrrolidine-1-carboxylic acid tert-butyl ester (1.2 g, 100%) as a colorless oil, MS: m/e 130.1 (M-OtBu).

EXAMPLE 124

(RS)-3-Acetylsulfanyl-pyrrolidine-1-carboxylic acid tert-butyl ester

To a 0° C. solution of triphenylphosphine (2.1 g, 8 mmol) in THF (14 ml) was added dropwise (15 minutes) diisopropylazodicarboxylate (1.55 ml, 8 mmol). After 30 minutes stirring at 0° C., a solution containing (RS)-3-hydroxy-pyrrolidine-1-carboxylic acid tert-butyl ester (1 g, 5.34 mmol) and thioacetic acid (0.57 ml, 8 mmol) in THF (7 ml) was added dropwise. The reaction mixture was stirred 30 minutes at 0° C., 45 minutes at room temperature and concentrated. The residue was chromatographed over silica gel (hexane-ethylacetate 9:1 then 8:2 then 1:1) to provide (RS)-3-acetylsulfanyl-pyrrolidine-1-carboxylic acid tert-butyl ester (1.4 g, 100%) as a slightly yellow oil, MS: m/e=246.3 (M+H$^+$).

(RS)-3-Hydroxy-pyrrolidine-1-carboxylic acid tert-butyl ester is a known compound and has been prepared as described in the following reference: M. Bouygues; M. Medou; G. Quelever; J. C. Chermann; M. Camplo; J. L. Kraus; Bioorg. Med. Chem. Lett.; 8; 3; 1998; 277–280.

EXAMPLE 125

(RS)-2-Indan-2-yl-oxirane

To a mixture containing NaH (9.8 mg, 0.2 mmol) and trimethylsulfoxoniumiodide (57.8 mg, 0.26 mmol) was added slowly DMSO (0.44 ml). After 30 minutes stirring at room temperature, a solution of indan-2-carbaldehyde (32 mg, 0.22 mmol) in DMSO (0.1 ml) was added. The reaction mixture was stirred 18 hours at room temperature and then quenched with $H_2O$. The aqueous phase was extracted with ethylacetate, combined organic phases were dried over $Na_2SO_4$, filtered and concentrated. The residue was chromatographed over silica gel (hexane-ethylacetate 98:2) to provide (RS)-2-indan-2-yl-oxirane (9 mg, 26%) as a colorless oil, MS: m/e=160.0 (M$^+$).

Indan-2-carbaldehyde is a known compound and has been prepared as described in the following reference: Kenner; J. Chem. Soc.; 105; 1914; 2694.

EXAMPLE 126 trans or cis-5-Phenyl-1-oxa-spiro[2.3]hexane see Example 127.

EXAMPLE 127 cis or trans-5-Phenyl-1-oxa-spiro[2.3]hexane

To a solution of (3-methylene-cyclobutyl)-benzene (0.236 g, 1.64 mmol) in $CH_2Cl_2$ (3 ml) was added successively methyltrioxorhenium (4 mg, 0.016 mmol), pyridine (15 □l, 0.2 mmol) and $H_2O_2$ (0.22 ml, 35% in $H_2O$). The reaction mixture was stirred 7 hours at room temperature, diluted with $CH_2Cl_2$, washed with $H_2O$, dried over $Na_2SO_4$ and concentrated. The residue was chromatographed over silica gel (hexane-ethylacetate 98:2) to provide the compound of example 126 trans or cis-5-phenyl-1-oxa-spiro[2.3]hexane (90 mg, first fraction, 35%) as a colorless oil, MS: m/e= 159.2 (M−H$^+$) and the compound of example 127 cis or trans-5-phenyl-1-oxa-spiro[2.3]hexane (56 mg, second fraction, 21%) as a colorless oil, MS: m/e=159.1 (M-H$^+$).

EXAMPLE 128

(3-Methylene-cyclobutyl)-benzene

To a 2–3° C. suspension of methyltriphenylphosphonium bromide (0.36 g, 1 mmol) in THF (2.5 ml) was added dropwise n-BuLi (0.69 ml, 1.1 mmol, 1.6 M in hexan). After 1 hour stirring at 0° C., a solution of 3-phenyl-cyclobutanone (0.146 g, 1 mmol) in THF (1.5 ml) was added dropwise. The reaction mixture was stirred 24 hours at room temperature and then diluted with hexane. The so obtained precipitate was filtered and the filtrate was concentrated. The residue was chromatographed over silica gel (hexane-ethylacetate 9:1) to provide (3-methylene-cyclobutyl)-benzene (57 mg, 40%) as a slightly yellow oil, MS: m/e=144.1 ($M^+$).

3-Phenyl-cyclobutanone is a known compound and has been prepared as described in the following reference: A. A. Frimer; J. Weiss; H. E. Gottlieb; J. L. Wolk; J. Org. Chem.; 59;4; 1994; 780–792.

EXAMPLE 129

3-Benzyl-cyclobutanone

A solution of (RS)-3-benzyl-2,2-dichlorocyclobutanone (0.3 g. 1.3 mmol) in acetic acid (3 ml) was refluxed for 1 hour in the presence of zinc (0.86 g, 13.1 mmol. powder). The reaction mixture was cooled to room temperature and filtered over decalite. The filtrate was neutralized with saturated $NaHCO_3$. The organic phase was washed successively with $H_2O$ and brine, dried over $Na_2SO_4$, and concentrated. The residue was chromatographed over silica gel (hexane-ethylacetate 4:1) to provide 3-benzyl-cyclobutanone (0.16 g, 76%) as a colorless oil, MS: m/e=160.2 ($M^+$).

EXAMPLE 130

(RS)-3-Benzyl-2,2-dichlorocyclobutanone

To a room temperature mixture containing allylbenzene (1.84 g, 15.6 mmol), zinc-copper couple (5.1 g, 78 mmol) and diethylether (60 ml) was added dropwise a solution of trichloroacetylchloride (2.96 ml, 26.5 mmol) and phosphorus oxychloride (2.46 ml, 26.5 mmol) in diethylether (20 ml). The reaction mixture was stirred at room temperature for 1 hour, filtered and the filtrate was partially concentrated. The residue was neutralized with saturated $NaHCO_3$. The aqueous phase was extracted with diethylether. The combined organic phases were washed successively with $H_2O$ and brine, dried over $Na_2SO_4$, and concentrated. The residue was chromatographed over silica gel (hexane) to provide (RS)-3-benzyl-2,2-dichlorocyclobutanone (0.71 g, 20%) as a yellow oil, MS: m/e=228.1 ($M-H^+$).

EXAMPLE 131

Toluene-4-sulfonic acid 4-phenyl-but-3-ynyl ester

A mixture containing 3-butyn-1-ol 4-methylbenzenesulfonate (0.45 g, 2 mmol), iodobenzene (0.45 g, 2.2 mmol), CuI (0.038 g, 0.2 mmol), triethylamine (1.01 g, 10 mmol) and tetrakis(triphenylphosphine) palladium (0.12 g, 0.1 mmol) in toluene (10 ml) was stirred 30 minutes at room temperature, and 2 hours at 65° C. The reaction mixture was cooled to room temperature, diluted with ethylacetate (10 ml), washed with $H_2O$ (10 ml), dried over $Na_2SO_4$, and concentrated. The residue was chromatographed over silica gel (hexane-ethylacetate 9:1 then 4:1) to provide toluene-4-sulfonic acid 4-phenyl-but-3-ynyl ester (0.35 g, 58%) as a brown oil, MS: m/e=300 ($M^+$).

3-Butyn-1-ol 4-methylbenzenesulfonate is a known compound and has been prepared as described in the following reference: E. Bonfand; W. B. Motherwell; A. M. K. Pennell; M. K. Uddin; F. Ujjainwalla; Heterocycles; 46; 1997; 523–534.

EXAMPLE 132

(2RS,3R)-2-Fluoro-1-[3-(4-hydroxy-phenylsulfanyl)-pyrrolidin-1-yl]-4-phenyl-butan-1-one (RS)-2-Fluoro-4-phenyl-butyric acid (0.66 g, 3.63 mmol) was dissolved in DMF (5 ml) and carbonyldiimidazole (0.64 g, 3.8 mmol) was added portionwise. After evolution of $CO_2$ has ceased, the reaction mixture was warmed to 55° C. for 20 minutes and then cooled to room temperature. A mixture of triethylamine (0.46 ml, 3.3 mmol) and (3R)-4-(pyrrolidin-3-ylsulfanyl)-phenol trifluoroacetic acid (1.02 g, 3.3 mmol) in DMF (5 ml) was added. The mixture was stirred at room temperature for 2 hours. The solvent was removed in vacuo and the residue taken up in $H_2O$ (30 ml).The mixture was extracted with ethylacetate (3×20 ml). The combined organic phases were dried over $Na_2SO_4$, filtered and the solvent was removed in vacuo. The residue was chromatographed over silica gel ($CH_2Cl_2$—MeOH, 99:1) to provide (2RS,3R)-2-fluoro-1-[3-(4-hydroxy-phenylsulfanyl)-pyrrolidin-1-yl]-4-phenyl-butan-1-one (1.12 g, 95%) as light yellow oil, MS: m/e=359.1($M^+$).

The preparation of (3R)-4-(pyrrolidin-3-yl-sulfanyl)-phenol trifluoroacetic acid is described in example 90.

Following the general method of example 132 the compound of example 133 was prepared.

EXAMPLE 133

(2RS,3S)-2-Fluoro-1-[3-(4-hydroxy-phenylsulfanyl)-pyrrolidin-1-yl]-4-phenyl-butan-1-one The title compound, MS: m/e=360.2 ($M+H^+$) was prepared from (RS)-2-fluoro-4-phenyl-butyric acid and (3S)-4-(pyrrolidin-3-yl-sulfanyl)-phenol hydrobromide.

EXAMPLE 134

(3S)-4-[1-(2.2-Difluoro-4-phenyl-butyl)-pyrrolidin-3-ylsulfanyl]-phenol

To a −60° C. solution of oxalylchloride (0.21 ml, 2.42 mmol) in dry $CH_2Cl_2$ (4 ml) was added a solution of DMSO (0.34 ml, 4.84 mmol) in $CH_2Cl_2$ (2 ml). After 5 minutes stirring, a solution of 2,2-difluoro-4-phenyl-butan-1-ol (0.41 g, 2.2 mmol) in $CH_2Cl_2$ was added dropwise at −60° C. After 15 minutes stirring, triethylamine (1.54 ml, 11 mmol) was added dropwise, the reaction mixture was allowed to warm up to room temperature and $H_2O$ (10 ml) was added. The aqueous phase was extracted with $CH_2Cl_2$ (3×20 ml).The combined organic phases were dried over $Na_2SO_4$, filtered and the solvent was removed in vacuo. The residue was dissolved in 1,2-dichloroethane (15 ml) and added to a suspension of (3S)-4-(pyrrolidin-3-ylsulfanyl)-phenol hydrobromide (0.68 g, 2.2 mmol), triethylamine (0.31 ml, 2.2 mmol) and sodium triacetoxyborohydride (0.74 g, 3.30 mmol) in 1,2-dichloroethane (45 ml). Mixture was stirred at 65° C. for 2 hours and overnight at room temperature. $H_2O$ (30 ml) was added. The aqueous phase was extracted with $CH_2Cl_2$ (3×20 ml).The combined organic phases were dried over $Na_2SO_4$, filtered and the solvent was removed in vacuo. The residue was chromatographed over silica gel (hexane-ethylacetate 99:1 to 90:10) to provide (3S)-4-[1-(2,2-difluoro-4-phenyl-butyl)-pyrrolidin-3-ylsulfanyl]-phenol (0.55 g, 70%) as light yellow oil, MS: m/e=364.2($M+H^+$).

Following the general method of example 134, the compound of example 135 was prepared.

EXAMPLE 135

(3R)-4-[1-(2,2-Difluoro-4-phenyl-butyl)-pyrrolidin-3-ylsulfanyl]-phenol

The title compound, MS: m/e=364.2 ($M+H^+$) was prepared from 2,2-difluoro-4-phenyl-butan-1-ol and (3R)-4-(pyrrolidin-3-ylsulfanyl)-phenol trifluoroacetic acid.

EXAMPLE 136

(RS)-2-Fluoro-4-phenyl-butyric acid (RS)-2-Fluoro-4-phenyl-butyric acid methyl ester (0.39 g, 2 mmol) was added to a solution of KOH (0.56 g, 10 mmol) in EtOH (5 ml). After 1 hour stirring at room temperature. the reaction mixture was concentrated, diluted with $H_2O$ (5 ml), acidified to pH 1 with 2N HCl and extracted with $CH_2Cl_2$ (3 times). The combined organic phases were dried over $Na_2SO_4$, filtered and concentrated to provide (RS)-2-fluoro-4-phenyl-butyric acid (0.343 g, 92%) as a colorless oil MS: m/e=182.1 ($M^+$).

The preparation of (RS)-2-fluoro-4-phenyl-butyric acid methyl ester is described example 122.

EXAMPLE 137

2,2-Difluoro-4-phenyl-butan-1-ol 2,2-Difluoro-4-phenyl-butyric acid ethyl ester (0.23 g, 1 mmol) was dissolved in EtOH (4 ml) and treated with $NaBH_4$ (39.4 mg, 1 mmol). After 30 minutes stirring at room temperature, the reaction mixture was cooled to 0° C., acidified to pH 1 with 1N HCl (2 ml), diluted with $H_2O$ (10 ml). The aqueous phase was extracted with ether (3 times). The combined organic phases were dried over $Na_2SO_4$, filtered and the solvent was removed in vacuo. The residue was chromatographed over silica gel (hexane-ethylacetate 99:1) to provide 2,2-difluoro-4-phenyl-butan-1-ol (0.11 g, 58%) as light yellow oil, MS: m/e=186.1 ($M^+$).

EXAMPLE 138

2,2-Difluoro-4-phenyl-butyric acid ethyl ester

Ethyl 2-oxo-4-phenylbutyrate (1 g, 4.7 mmol) was treated with (diethylamino)sulfur trifluoride (1.3 ml, 9.4 mmol). After 2 hours stirring at room temperature, the reaction mixture was poured on $H_2O$-ice. The aqueous phase was extracted with $CH_2Cl_2$ (2 times). The combined organic phases were washed with $H_2O$, dried over $Na_2SO_4$, filtered and the solvent was removed in vacuo. The residue was distilled to provide 2,2-difluoro-4-phenyl-butyric acid ethyl ester (1.0 g, 94%) as yellow oil, MS: m/e=228.1 ($M^+$), b.p.: 90° C., 0.2 mbar. Ethyl 2-oxo-4-phenylbutyrate is a commercially available compound.

EXAMPLE A

| | Tablet Formulation (Wet Granulation) | | | | |
|---|---|---|---|---|---|
| Item | Ingredients | | mg/tablet | | |
| 1. | Compound of formula 1 | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

EXAMPLE B

| | Capsule Formulation | | | | |
|---|---|---|---|---|---|
| Item | Ingredients | | mg/tablet | | |
| 1. | Compound of formula 1 | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2, and 3 in a suitable mixer for 30 minutes.
2. Add items 4 and 5 and mix for 3 minutes.
3. Fill into a suitable capsule.
4. Add item 5 and mix for three minutes; compress on a suitable press.

What is claimed is:

1. A compound of formula

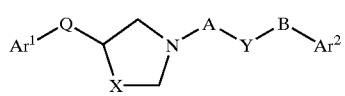

I wherein $Ar^1$ is selected from the group consisting of pyridyl and phenyl, pyridyl and phenyl substituted by hydroxy, lower alkyl, halogen, amino, nitro, benzyloxy or lower alkoxy-lower alkoxy, and the group

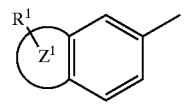

wherein $Z^1$ is a five membered heterocyclic ring, which contains one or two heteroatoms, selected from N or O;

$R^1$ is selected from hydrogen, hydroxy and an oxo group;

$Ar^2$ is selected from the group consisting of pyridyl and phenyl, pyridyl and phenyl optionally substituted by hydroxy, lower alkyl, halogen, amino, nitro, benzyloxy or lower alkoxy-lower alkoxy, and the group

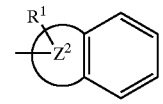

wherein $Z^2$ is a five or six membered ring, a five or six membered ring which optionally contains one or two heteroatoms, selected from N or O; and Q is —S—, —S(O)— or —S(O)$_2$—;

X is a bond, —CH(OH)— or —(CH$_2$)$_n$—;

A is a bond or —(CHR)$_m$—;

R is selected from hydrogen, halogen or hydroxy, independently from each other if m is 2 or 3;

Y is selected from —(CR$_2$)$_m$—, —O—, —C═C—, —C≡C—, piperidin-1-yl, pyrrolidin-1-yl or $C_4$–$C_6$- cycloalkyl, and piperidin-2-yl, pyrrolidin-1-yl or $C_4$–$C_6$-cycloalkyl rings substituted by hydroxy;

B is a bond, —O— or —(CHR)$_m$;

n is 1 or 2; and m is 1, 2 or 3;

and pharmaceutically acceptable acid addition salts thereof with the exception of compounds, wherein A and B are simultaneously a bond Y is —CHR—.

2. A compound according to claim 1, wherein Ar$^1$ is phenyl, substituted by hydroxy, Q is —S—, Ar$^2$ is phenyl and X is —CH$_2$—.

3. A compound according to claim 2, which is
(S)-4-[1-(4-phenyl-butyl)-pyrrolidin-3-yl-sulfanyl]-phenol,
(RS)-4-[1-(4-phenyl-butyl)-pyrrolidin-3-yl-sulfanyl]-phenol,
(R)-4-[1-(4-phenyl-butyl)-pyrrolidin-3-yl-sulfanyl]-phenol,
(2R,3S) or (2S,3S)-4-[1-(2-hydroxy-4-phenyl-butyl)-pyrrolidin-3-yl-sulfanyl]-phenol,
(2S,3S) or (2R,3S)-4-[1-(2-hydroxy-4-phenyl-butyl)-pyrrolidin-3-yl-sulfanyl]-phenol,
(RS)-4-[1-(3-phenyl-propyl)-pyrrolidin-3-yl-sulfanyl]-phenol,
(3RS,3RS) and (3RS,3SR)-4-[1-(3-hydroxy-4-phenyl-butyl)-pyrrolidin-3-yl-sulfanyl]-phenol,
(2S,3R) or (2R,3R)-4-[1-(2-hydroxy-4-phenyl-butyl)-pyrrolidin-3-yl-sulfanyl]-phenol,
(2RS,3S)-4-[1-(2-fluoro-4-phenyl-butyl)-pyrrolidin-3-yl-sulfanyl]-phenol or
(2RS ,3R)-4-[1-(2-fluoro-4-phenyl-butyl)-pyrrolidin-3-yl-sulfanyl]-phenol.

4. A compound according to claim 3 wherein the compound is (S)-4-[1-(4-phenyl-butyl)-pyrrolidin-3-yl-sulfanyl]-phenol.

5. A compound according to claim 3 wherein the compound is (2RS,3S)-4-[1-(2-Fluoro-4-phenyl-butyl)-pyrrolidin-3-ylsulfanyl]-phenol.

6. A compound according to claim 3 wherein the compound is (R)-4-[1-(4-Phenyl-butyl)-pyrrolidin-3-yl-sulfanyl]-phenol.

7. A compound according to claim 1, wherein Ar$^1$ is phenyl, substituted by hydroxy, Q is —S(O)—, Ar$^2$ is phenyl and X is —CH$_2$.

8. A compound according to claim 7, which is selected from the group consisting of
(3RS,S-oxide RS) and (3RS,S-oxide SR)-4-[1-(4-phenyl-butyl)-pyrrolidine-3-sulfinyl]-phenol,
(2R,3R, S-oxide R)-4-[1-(2-fluoro-4-phenyl-butyl)-pyrrolidine-3-sulfinyl]-phenol,
(2S,3S,S-oxide R)-4-[1-(2-fluoro-4-phenyl-butyl)-pyrrolidine-3-sulfinyl]-phenol,
(2R,3S,S-oxide R)-4-[1-(2-fluoro-4-phenyl-butyl)-pyrrolidine-3-sulfinyl]-phenol or
(3S,S-oxide S) or (3S,S-oxide R)-4-[1-(2,2-difluoro-4-phenyl-butyl)-pyrrolidine-3-sulfinyl]-phenol.

9. The compound of claim 8 wherein the compound is (2S,3S,S-oxide R)-4-[1-(2-Fluoro-4-phenyl-butyl)-pyrrolidine-3-sulfinyl]-phenol.

10. A compound according to claim 1, wherein Ar$^1$ is phenyl, substituted by hydroxy, Q is —S(O)$_2$—, Ar$^2$ is selected from the group consisting of indanyl, phenyl, and indanyl and phenyl substituted by methyl wherein X is —CH$_2$— or —CH(OH)—.

11. A compound according to claim 10, which is selected from the group consisting of (S)-4-[1-(4-phenyl-butyl)-pyrrolidine-3-sulfonyl]-phenol,
(RS)-4-[1-(4-phenyl-butyl)-pyrrolidine-3-sulfonyl]-phenol,
(2R,3S) and (2S,3S)-4-[1-(2-fluoro-4-phenyl-butyl)-pyrrolidine-3-sulfonyl]-phenol,
(3RS,cis) and (3RS,trans)-4-[1-(3-benzyl-cyclobutyl)-pyrrolidine-3-sulfonyl]-phenol,
(3RS,cis)-4-[1-(4-phenyl-cyclohexyl)-pyrrolidine-3-sulfonyl]-phenol,
(3RS ,4RS)-4-(4-hydroxy-benzenesulfonyl)-1-(4-phenyl-butyl)-pyrrolidin-3-ol,
(RS)-4-[1-(4-m-tolyl-butyl)-pyrrolidine-3-sulfonyl]-phenol,
(RS)-4-[1-(3-phenyl-propyl)-pyrrolidine-3-sulfonyl]-phenol,
(R)-4-[1-(4-phenyl-butyl)-pyrrolidine-3-sulfonyl]-phenol,
(RS)-4-[1-(1-phenyl-piperidin-4-yl)-pyrrolidine-3-sulfonyl]-phenol or
(2R,3S) or (2S,3S)-4-[1-(2-hydroxy-4-phenyl-butyl)-pyrrolidine-3-sulfonyl]-phenol.

12. A compound according to claim 11, wherein the compound is selected from the group consisting of (2R,3S) and (2S,3S)-4-[1-(2-Fluoro-4-phenyl-butyl)-pyrrolidine-3-sulfonyl]-phenol.

13. A compound according to claim 11 wherein the compound is selected from the group consisting of (3RS,cis) and (3RS,trans)-4-[1-(3-Benzyl-cyclobutyl)-pyrrolidine-3-sulfonyl]-phenol.

14. A compound according to claim 11 wherein the compound is (3RS,cis)-4-[1-(4-phenyl-cyclohexyl)-pyrrolidine-3-sulfonyl]-phenol>.

15. A compound according to claim 11 wherein the compound is selected from the group consisting of (2R,3S) and (2S,3S)-4-[1-(2-Hydroxy-2-indan-2-yl-ethyl)-pyrrolidine-3-sulfonyl]-phenol.

16. A compound according to claim 11 wherein the compound is (3RS,4RS)-4-(4-hydroxy-benzenesulfonyl)-1-(4-phenyl-butyl)-pyrrolidin-3-ol.

17. A method of treating over-activation of NMDA receptors in a disease selected from neurodegeneration caused by stroke or brain trauma, or chronic forms of neurodegeneration caused by Alzheimer's disease, Parkinson's disease, Huntington's disease, ALS (amyotrophic lateral sclerosis), bacterial or viral infections comprising administering to a patient in need thereof a therapeutically effective amount of a compound of claim 1.

18. A pharmaceutical composition for treating over-activation of NMDA receptors comprising a therapeutically effective amount of a compound of claim 1.

* * * * *

UNITED STATES PATENT AND TRADEMARK OFFICE
CERTIFICATE OF CORRECTION

PATENT NO.     : 6,451,819 B2
DATED          : September 17, 2002
INVENTOR(S)    : Alexander Alanine et al.

It is certified that error appears in the above-identified patent and that said Letters Patent is hereby corrected as shown below:

Column 45,
Line 8, insert -- and -- between "bond" and "Y".

Signed and Sealed this

Eleventh Day of February, 2003

JAMES E. ROGAN
*Director of the United States Patent and Trademark Office*